United States Patent
Kanayama et al.

(10) Patent No.: US 8,315,681 B2
(45) Date of Patent: Nov. 20, 2012

(54) METHOD FOR NONINVASIVE MEASUREMENT OF GLUCOSE AND APPARATUS FOR NONINVASIVE MEASUREMENT OF GLUCOSE

(75) Inventors: Shoichi Kanayama, Otawara (JP); Omar S. Khalil, Chicago, IL (US); Tzyy-Wen Jeng, Vernon Hills, IL (US); Shu-Jen Yeh, Glencoe, IL (US)

(73) Assignee: Toshiba Medical Systems Corporation, Otawara-shi (JP)

( * ) Notice: Subject to any disclaimer, the term of this patent is extended or adjusted under 35 U.S.C. 154(b) by 687 days.

(21) Appl. No.: 12/418,899

(22) Filed: Apr. 6, 2009

(65) Prior Publication Data

US 2010/0016689 A1 Jan. 21, 2010

Related U.S. Application Data

(63) Continuation of application No. 12/059,522, filed on Mar. 31, 2008, now abandoned, which is a continuation of application No. PCT/JP2006/323995, filed on Nov. 30, 2006.

(30) Foreign Application Priority Data

Nov. 30, 2005 (JP) ................................. 2005-347194
May 8, 2006 (JP) ................................. 2006-129490

(51) Int. Cl.
*A61B 5/1455* (2006.01)
(52) U.S. Cl. ........................................................ 600/316
(58) Field of Classification Search .................. 600/310, 600/316, 334
See application file for complete search history.

(56) References Cited

U.S. PATENT DOCUMENTS

| 3,628,525 | A | 12/1971 | Polanyi |
| 4,259,963 | A | 4/1981 | Huch |
| 4,432,365 | A | 2/1984 | Leist |
| 4,890,619 | A | 1/1990 | Hatschek |
| 4,926,867 | A | 5/1990 | Kanda |
| 5,028,787 | A | 7/1991 | Rosenthal |

(Continued)

FOREIGN PATENT DOCUMENTS

EP  1 459 679  9/2004

(Continued)

OTHER PUBLICATIONS

Airat K. Amerov, et al., "Molar Absorptivities of Glucose and Other Biological Molecules in Aqueous Solutions over the First Overtone and Combination Regions of the Near-Infrared Spectrum", Applied Spectroscopy, vol. 58, No. 10, 2004, 5 Pages.

(Continued)

*Primary Examiner* — Eric Winakur
(74) *Attorney, Agent, or Firm* — Oblon, Spivak, McClelland, Maier & Neustadt, L.L.P.

(57) ABSTRACT

A method for noninvasive measurement of glucose in a tissue of a subject, including the steps of bringing an adaptation device, which has a shape similar to a measurement probe, into contact with a skin part of a subject for stretching the skin part of the subject under a pressure that is higher than a pressure per unit area applied by the measurement probe during the noninvasive measurement, maintaining the contact for a predetermined period of time followed by relieving the contact, bringing the measurement probe into contact with the stretched skin part of the subject for the noninvasive measurement, collecting signals emitted from the subject, and estimating a glucose concentration based on the collected signals.

7 Claims, 14 Drawing Sheets

U.S. PATENT DOCUMENTS

| | | | |
|---|---|---|---|
| 5,068,536 | A | 11/1991 | Rosenthal |
| 5,077,476 | A | 12/1991 | Rosenthal |
| 5,086,229 | A | 2/1992 | Rosenthal |
| 5,131,391 | A | 7/1992 | Sakai |
| 5,237,178 | A | 8/1993 | Rosenthal |
| 5,324,979 | A | 6/1994 | Rosenthal |
| 5,360,004 | A | 11/1994 | Purdy |
| 5,379,764 | A | 1/1995 | Barnes |
| 5,460,177 | A | 10/1995 | Purdy |
| 5,492,118 | A | 2/1996 | Gratton |
| 5,551,422 | A | 9/1996 | Simonsen |
| 5,576,544 | A | 11/1996 | Rosenthal |
| 5,636,633 | A | 6/1997 | Messerschmidt |
| 5,655,530 | A | 8/1997 | Messerschmidt |
| 5,703,364 | A | 12/1997 | Rosenthal |
| 5,747,806 | A | 5/1998 | Khalil |
| 5,795,305 | A | 8/1998 | Cho |
| 5,924,996 | A | 7/1999 | Cho |
| 5,940,182 | A | 8/1999 | Lepper, Jr. |
| 5,945,676 | A | 8/1999 | Khalil |
| 5,957,841 | A | 9/1999 | Maruo |
| 5,978,691 | A | 11/1999 | Mills |
| 6,016,435 | A | 1/2000 | Maruo |
| 6,049,081 | A | 4/2000 | Sterling |
| 6,230,034 | B1 | 5/2001 | Messerschmidt |
| 6,280,381 | B1 | 8/2001 | Malin |
| 6,534,012 | B1 | 3/2003 | Hazen et al. |
| 6,556,850 | B1 | 4/2003 | Braig |
| 6,954,661 | B2 | 10/2005 | Cho et al. |
| 7,043,287 | B1 * | 5/2006 | Khalil et al. ............... 600/316 |
| 2002/0038080 | A1 | 3/2002 | Makarewicz et al. |
| 2002/0055671 | A1 | 5/2002 | Wu et al. |
| 2003/0023151 | A1 | 1/2003 | Khalil et al. |
| 2004/0167382 | A1 | 8/2004 | Gardner et al. |
| 2005/0124868 | A1 | 6/2005 | Cho |

FOREIGN PATENT DOCUMENTS

| | | |
|---|---|---|
| EP | 1 484 006 A1 | 12/2004 |
| EP | 1 537 822 | 6/2005 |
| EP | 1 595 493 A1 | 11/2005 |
| JP | 7-284490 | 10/1995 |
| JP | 11-47119 | 2/1999 |
| JP | 11-510417 | 9/1999 |
| JP | 2002-527180 | 8/2002 |
| JP | 2004-283585 | 10/2004 |
| JP | 2004-531311 | 10/2004 |
| JP | 2004-535213 | 11/2004 |
| JP | 2006-182 | 1/2006 |
| WO | WO 99/59464 | 11/1999 |
| WO | WO 01/87151 A2 | 11/2001 |
| WO | WO 02/060320 A1 | 8/2002 |
| WO | WO 02/082989 A1 | 10/2002 |
| WO | WO 2007/063961 A1 | 6/2007 |

OTHER PUBLICATIONS

M. Ries Robinson, et al., "Noninvasive Glucose Monitoring in Diabetic Patients: A Preliminary Evaluation", Clinical Chemistry, vol. 38, No. 9, 1992, pp. 1618-1622.

John S. Maier, et al., "Possible correlation between blood glucose concentration and the reduced scattering coefficient of tissues in the near infrared", Optics Letters, vol. 19, No. 24, Dec. 15, 1994, pp. 2062-2064.

Matthias Kohl, et al., "Influence of glucose concentration on light scattering in tissue-simulating phantoms", Optics Letters, vol. 19, No. 24, Dec. 15, 1994, 2 Pages.

Matthias Kohl, et al., "The Influence of glucose concentration upon the transport of light in tissue-simulating phantoms", Phys. Med. Biol., vol. 40, 1995, pp. 1267-1287.

Lutz Heinemann, et al., "Noninvasive Glucose Measurement by Monitoring of Scattering Coefficient During Oral Glucose Tolerance Tests", Diabetes Technology & Therapeutics, vol. 2, No. 2, 2000, pp. 211-220.

Jan Laufer, et al., "Effect of temperature on the optical properties of ex vivo human dermis and subdermis", Phys. Med. Biol., vol. 43, 1998, 6 Pages.

J. T. Bruulsema, et al., "Optical Properties of Phantoms and Tissue Measured in vivo from 0.9-1.3 µm using Spatially Resolved Diffuse Reflectance", SPIE Proceedings, vol. 2979, 1997, pp. 325-334.

Omar S. Khalil, et al., "Temperature modulation of the visible and near infrared absorption and scattering coefficients of human skin", Journal of Biomedical Optics, vol. 8, No. 2, Apr. 2003, pp. 191-205.

Shu-jen Yeh, et al., "Near-infrared thermo-optical response of the localized reflectance of intact diabetic and nondiabetic human skin", Journal of Biomedical Optics, vol. 8, No. 3, Jul. 2003, pp. 534-544.

Shu-jen Yeh, et al., "Monitoring Blood Glucose Changes in Cutaneous Tissue by Temperature-modulated Localized Reflectance Measurements", Clinical Chemistry, vol. 49, No. 6, 2003, pp. 924-934.

Omar S. Khalil, et al., "Response of near IR localized reflectance signals of intact diabetic human skin to thermal stimuli", SPIE Proceedings, vol. 5068, 2003, pp. 142-148.

Ok Kyung Cho, et al., "Noninvasive Measurement of Glucose by Metabolic Heat Conformation Method", Clinical Chemistry, vol. 50, No. 10, 2004, pp. 1894-1898.

Jae B. Ko, et al., "Body Metabolism provides a Foundation for Noninvasive Blood Glucose Monitoring", Diabetes Care, vol. 27, No. 5, May 2004, pp. 1211-1212.

Carl D. Malchoff, et al., "A Novel Noninvasive Blood Glucose Monitor", Diabetes Care, vol. 25, No. 12, Dec. 2002, pp. 2268-2275.

Partial European Search Report issued Nov. 10, 2010, in Patent Application No. 10170622.4.

Office Action issued Sep. 20, 2011, in Japanese Patent Application No. 2006-129490 (with English-language translation).

Office Action issued Jan. 17, 2012, in Japanese Patent Application No. 2006-129490 with English translation.

European Search Report issued Sep. 19, 2012 in connection with European Application No. 11180748, filed Nov. 30, 2006.

European Search Report issued Sep. 28, 2012 in connection with corresponding European Application No. 11 18 0771, filed Nov. 30, 2006.

* cited by examiner

METHOD FOR NONINVASIVE MEASUREMENT OF GLUCOSE AND APPARATUS FOR NONINVASIVE MEASUREMENT OF GLUCOSE

CROSS REFERENCE TO RELATED APPLICATIONS

This is a Continuation Application of PCT Application No. PCT/JP2006/323995, filed Nov. 30, 2006, which was published under PCT Article 21(2) in Japanese.

This application is based upon and claims the benefit of priority from prior Japanese Patent Applications No. 2005-347194, filed Nov. 30, 2005; and No. 2006-129490, filed May 8, 2006, the entire contents of both of which are incorporated herein by reference.

This application is a Continuation application of U.S. application Ser. No. 12/059,522, pending.

BACKGROUND OF THE INVENTION

1. Field of the Invention

The present invention relates to an apparatus and a method for noninvasive measurement, with which glucose in a subject is noninvasively measured optically through a measurement probe.

2. Description of the Related Art

In several prior art methods, noninvasive (NI) measurement of glucose concentration in a subject is described. This measurement method generally includes the steps of: bringing an optical probe into contact with a body part; performing a series of optical measurements; and collecting a series of light signals. Subsequently, these light signals or derived optical parameters are mutually associated with blood glucose concentrations for the establishing a calibration relationship. A glucose concentration is determined by a subsequent measurement using the light signals measured at that time and the previously established calibration relationship.

The method for noninvasive (NI) measurement of glucose is classified into two broad categories: one is a method of tracking molecular properties; and the other is a method of tracking the effect of glucose on tissue properties. The method in the first category includes tracking intrinsic properties of glucose such as near-infrared (NIR) absorption coefficients, mid-infrared absorption coefficients, optical rotations, Raman shift band and NIR photoacoustic absorption. Such a method is based on an ability to detect glucose in a tissue or blood independently of other analytes of the body and also physiological conditions of the body. The method of the second type is based on the measurement of the effect of glucose on optical properties of tissue such as scattering coefficients of tissue, refractive index of interstitial fluid (ISF) or sound propagation in tissue.

The method of the first type of tracking the molecular properties of glucose faces a big problem because a signal which can be considered to be specific for glucose is extremely weak. Biological noise, a person-to-person difference, and measurement noise may drown out a small change in signal specific for glucose. In order to extract glucose-related information from a data set with noise, a multivariate analysis has been commonly used. The method of the second type of tracking the effect of glucose on tissue properties instead of the intrinsic molecular properties of glucose faces a big problem because of a nonspecific property of the change in parameters to be measured.

The method of both types of tracking the molecular properties of glucose and the effect of glucose on tissue properties ignores the physiological response of the body to a change in glucose concentration. This response can be seen in the form of a change in blood flow or temperature. Such a change in blood flow or temperature as a result of the physiological response of the body affects NIR light signals. The measurement by the method of both types also ignores the effect of the body-probe interaction on signals measured, and further, a specific time window for data collection from the initiation of the body-probe interaction is not defined.

Absorption Method:

Patent documents 1, 2, 3, 4, 5, 6, 7 and 8 describe a method in which glucose is measured by bringing an optical probe into contact with a body part and also reflection or transmission signals in near-infrared (NIR) region ranging from 600 to 1100 nm are measured. In general, a blood-containing body part (such as a finger) is illuminated with one or more light wavelengths, and one or more detectors detect the light passing through the body part. A glucose level is derived from the comparison of the reference spectrum of glucose and the background interference. These patents do not deal with the physiological response of the body to a change in glucose concentration, or the tissue-probe adaptation effect on the light signals measured.

In patent documents 9, 10 and 11, measurement of glucose NIR signals at a long wavelength ranging from 1000 to 1800 nm has been claimed. These patents disclose a method in which an extremely low signal is tried to be measured in the presence of biological noise which is much larger than the signal. The method of these patents does not provide temperature modulation at the measurement site, and these patents do not deal with the physiological response to a change in glucose concentration or the response of the body to the probe when the body and the probe interact with each other during the measurement.

Patent documents 12 to 19 disclose a method for NI measurement of glucose using NIR reflectance and transmittance measurement at a wavelength ranging from 1000 to 2000 nm. These patents do not deal with the physiological response of the body to glucose or problems of the probe-tissue interaction, or describe the application of temperature stimulation.

An example of the magnitude of NIR glucose intrinsic absorption signals is illustrated by the recently measured values of the molar extinction coefficient $\epsilon$ of glucose in water reported in the article in the journal (Non-patent document 1). The absorption ratio of glucose in water was determined to be 0.463 $M^{-1}$ $cm^{-1}$ at 1689 nm, 0.129 $M^{-1}$ $cm^{-1}$ at 2270 nm and 0.113 $M^{-1}$ $cm^{-1}$ at 2293 nm (here, M represents a molar concentration). These values of absorption ratios are much smaller than the $\epsilon$ value of NADH at 340 nm being $6.2\times10^{+3}$ $mol^{-1}$ $cm^{-1}$, which is commonly used for the measurement of serum glucose values with an automated blood analyzer. When a 1 mm pathlength is used, a 10 mM glucose solution has $4.63\times10^{-4}$ absorbance units at 1686 nm, and $1.29\times10^{-4}$ absorbance units at 2257 nm. The 1 mm pathlength is longer than the pathlength encountered in the NIR diffuse reflectance measurement, and has a magnitude comparable to the pathlength in the localized reflectance measurement. The intrinsic extinction coefficient of glucose has a magnitude much lower at the higher overtone bands between 800 nm and 1300 nm than that at 2200 nm. The quantitative interpretation of data in this spectral range requires an extremely high sensitive detection system with a high signal to noise ratio and tight temperature modulation, and elimination of biological background noise source. Although IR absorption measurement of glucose has reasonable specificity in aqueous solutions, it faces a serious problem when attempted at the body sites of a subject.

The earliest report of use of measurement of NIR absorption and reflectance was reported in 1992 (Non-patent document 2), however, a commercially available device for noninvasive measurement of glucose by NIR has been unavailable so far.

Scattering Method:

Patent document 20 by Simonsen et al. and Patent document 21 by Gratton et al. disclose a method of measuring a scattering coefficient in deep tissue structures such as calf muscle and abdominal area. The geometric arrangement of a measurement probe, a distance between a light source and a detecting point, and the use of diffusion approximation in a light transport equation require light sampling at a depth of about several centimeters in a tissue.

A scattering method for NI measurement of glucose is described in the articles in the literatures of Non-patent documents 3, 4, and 5. In the method using the effect of glucose on the magnitude of a tissue scattering coefficient, a change in refractive index of interstitial fluid (ISF) which is resulted from a change in glucose concentration is tracked. The effect of a solute concentration on the refractive index of a solution is not specific for a given compound. A change in other soluble metabolite and electrolyte concentrations or tissue hydration affects the refractive index in the same manner as a change in glucose concentration. The reported clinical results have showed that there is no specificity and it is impossible to predict a glucose concentration (Non-patent document 6).

The effect of changing temperature on tissue scattering and absorption properties has been very interesting in noninvasive monitoring techniques. This has been reported in a few articles in journals. Please see Non-patent documents 7 and 8. The effect of temperature on the optical properties of the human skin has been reported in the articles in the journals of Non-patent documents 9, 10, 11 and 12. These published reports show a reversible linear change in scattering coefficient of the human skin after changing the temperature, and a more irreversible change in skin absorption coefficient after changing the temperature.

Thermal Radiation Method:

Other patents and patent application publications disclose a method which depends on IR radiation from a subject. In Patent documents 22 and 23 by Sterling et al., altered thermal IR radiation was used for NI measurement of glucose. The use of metabolic thermal radiation from a subject as means for glucose measurement has been disclosed in Patent documents 24 and 25 by Cho et al., and Patent document 26 (June, 2005) and Patent document 27 (June, 2005). A few experimental data have been disclosed in the articles in the journals: Non-patent documents 13 and 14. Cho et al. did not separate the circadian effect of the body which causes a temperature change from a change in glucose concentration which may cause a temperature change in a similar manner. Cho et al. did not take the skin-probe adaptation effect on the optical or thermal signals into consideration, or did not generate a temperature change that affects glucose metabolism.

Patent document 28 by Buchert and the article of the journal of Non-patent document 15 describe a method for NI measurement of glucose based on a spectral analysis of IR radiation from the tympanic membrane. Buchert and Malchoff et al. did not induce a temperature change for affecting glucose metabolism.

The use of a temperature change in combination with optical measurement with respect to a subject is described in other NI optical measurements. Patent documents 29, 30, 31, 32, 33 and 34 describe an oximeter probe having a heating element designed such that it is disposed against a body part. In Patent document 35, a glucose sensor which is brought to a specified temperature and in which a scattering coefficient $\mu_s'$ is calculated is described and a glucose concentration is estimated from the effect on the refractive index of interstitial fluid (ISF). Patent document 35 does not disclose the calculation of oxygen consumption as a result of the physiological effect of glucose metabolism, or describe the use of temperature-enhanced glucose metabolism, or disclose the use of time window for reducing the tissue-probe adaptation effect on the measurement to the minimum.

Patent document 36 by Mills describes a method for measuring blood parameters at various temperatures based on the measurement of diffuse reflectance or transmission. Patent document 36 does not disclose the calculation of oxygen consumption as a result of the physiological effect of glucose metabolism, or describe the use of temperature-enhanced glucose metabolism, or take the time window for reducing the tissue-probe adaptation effect on the measurement to the minimum into consideration.

Although there are a variety of prior art and a large number of published patents in the past 10 years, however, any of the methods of noninvasive detection of glucose in a human tissue was not commercially successful. Accordingly, a method for noninvasive measurement of glucose in a subject which overcomes the problems of the signal magnitude and specificity, and without resorting to insertion of a probe or extraction of a sample has been still needed.

Further, several prior art methods for noninvasive (NI) quantification of the concentration of an analyte, particularly glucose in a subject generally includes the steps of: bringing a measurement probe into contact with a body part; performing a series of optical measurements; and collecting a set of light signals. These light signals or derived optical parameters calculated from the signals are mutually associated with blood glucose concentrations for establishing a calibration relationship. A glucose concentration is determined by a subsequent measurement using the light signals measured at that time and the previously established calibration relationship.

The method for noninvasive (NI) determination of glucose is classified into two broad categories: one is a method of tracking molecular properties; and the other is a method of tracking the effect of glucose on tissue properties. The method in the first category includes tracking intrinsic properties of glucose such as near-infrared (NIR) absorption coefficients, mid-infrared absorption coefficients, optical rotations, Raman shift band and NIR photoacoustic absorption. Such a method is based on an ability to detect glucose in a tissue or blood independently of other analytes of the body and also physiological conditions of the body. The method of the second type depend on the measurement of the effect of glucose on optical properties of tissue such as scattering coefficients of tissue, refractive index of interstitial fluid (ISF) or sound propagation in tissue.

The method of the first type of tracking the molecular properties of glucose encounters an extremely weak signal which can be considered to be specific for glucose. Biological noise, a person-to-person variation, and measurement noise may drown out a small change in the signal specific for glucose. In order to extract glucose-related information from a data set with noise, a multivariate analysis has been commonly used. The method of the second type of tracking the effect of glucose on tissue properties faces a big problem because of a nonspecific property of the change in refractive index calculated from the change in scattering coefficient.

In either type of methods, the intensity of the detected signal is extremely smaller than that of the biological and bodily interface noise. The variable probe-skin interaction which is attributable to the variation in the interface between a probe and the body, and a variable contact between a measurement probe and the skin due to the error of repositioning of the probe can have an effect on a measured signal which is larger than an effect on a change in glucose concentration.

The prior art method of both types of tracking the molecular properties of glucose and the effect of glucose on tissue properties ignores the effect of the body-probe interaction on the measured signal, and a method for reducing this effect is not described. As a result, a reference value of glucose is generally applied (fitted) to a signal adversely affected by an optical effect of an interaction between a probe and the skin or a probe and a body part.

Patent documents 37 to 44 describe a light absorption method for measuring reflection or transmission signals in near-infrared (NIR) region ranging from 600 to 1100 nm for measuring glucose by bringing a measurement probe into contact with a body part. In general, a blood-containing body part (such as a finger or a skin region of an arm) is illuminated with one or more wavelength lights, and one or more detectors detect the light passing through the body part or reflecting from the body part. A glucose level is derived from the comparison of the reference spectrum of glucose and the background interference. These patent documents do not deal with the tissue-probe adaptation effect on the light signals measured.

In Patent documents 45, 46 and 47, measurement of glucose NIR signals at a long wavelength ranging from 1000 to 1800 nm has been claimed. The method of these patent documents does not deal with a reaction of the skin with a measurement probe when the measurement probe interacts with the skin during measurement.

Patent documents 48, 49 and 50 transferred to Sensys Medical, Patent documents 51 and 52 transferred to Matsushita, and Patent documents 53, 54 and 55 transferred to Inlight Solutions disclose a method for NI quantification of glucose using measurement of NIR reflectance and transmission at a wavelength ranging from 1000 to 2000 nm. These patent documents do not deal with problems of the probe-tissue interaction, particularly adaptation of the skin to a probe and a variability of contact between the skin and a measurement probe.

Patent document 56 by Simonsen et al. and Patent document 57 by Gratton et al. disclose a method for measuring a bulk scattering coefficient in deep tissue structures such as calf muscle and abdominal area. The published clinical results show that it lacks specificity and glucose concentration cannot be predicted (Non-patent document 16). A drift (change) in the signal independent of glucose was observed, and it was larger than a change in scattering coefficient due to a change in glucose concentration in some cases.

In Patent document 56, a glucose sensor that is brought to a specified temperature is described and a bulk scattering coefficient is calculated, and a glucose concentration is estimated from the effect on the refractive index of interstitial fluid (ISF). Patent document 56 does not disclose a method for reducing the effect of tissue-probe adaptation on the measurement to the minimum.

Patent document 58 by Mills describes a method for measuring blood parameters at various temperatures based on the measurement of diffuse reflectance or transmission. Patent document 58 does not disclose a method for reducing the effect of tissue-probe adaptation on the measurement to the minimum.

Patent document 1: U.S. Pat. No. 5,077,476
Patent document 2: U.S. Pat. No. 5,068,536
Patent document 3: U.S. Pat. No. 5,576,544
Patent document 4: U.S. Pat. No. 5,703,364
Patent document 5: U.S. Pat. No. 5,028,787
Patent document 6: U.S. Pat. No. 5,086,229
Patent document 7: U.S. Pat. No. 5,324,979
Patent document 8: U.S. Pat. No. 5,237,178
Patent document 9: U.S. Pat. No. 5,360,004
Patent document 10: U.S. Pat. No. 5,460,177
Patent document 11: U.S. Pat. No. 5,379,764
Patent document 12: U.S. Pat. No. 5,747,806
Patent document 13: U.S. Pat. No. 5,945,676
Patent document 14: U.S. Pat. No. 6,280,381
Patent document 15: U.S. Pat. No. 5,957,841
Patent document 16: U.S. Pat. No. 6,016,435
Patent document 17: U.S. Pat. No. 5,636,633
Patent document 18: U.S. Pat. No. 5,655,530
Patent document 19: U.S. Pat. No. 6,230,034
Patent document 20: U.S. Pat. No. 5,551,422
Patent document 21: U.S. Pat. No. 5,492,118
Patent document 22: U.S. Pat. No. 6,049,081
Patent document 23: U.S. Pat. No. 6,556,850
Patent document 24: U.S. Pat. No. 5,795,305
Patent document 25: U.S. Pat. No. 5,924,996
Patent document 26: US Patent Application Publication No. 2005/0124868
Patent document 27: European Patent Application Publication No. 1537822
Patent document 28: U.S. Pat. No. 5,940,182
Patent document 29: U.S. Pat. No. 3,628,525
Patent document 30: U.S. Pat. No. 4,259,963
Patent document 31: U.S. Pat. No. 4,432,365
Patent document 32: U.S. Pat. No. 4,890,619
Patent document 33: U.S. Pat. No. 4,926,867
Patent document 34: U.S. Pat. No. 5,131,391
Patent document 35: U.S. Pat. No. 5,551,422
Patent document 36: U.S. Pat. No. 5,978,691
Patent document 37: U.S. Pat. No. 5,077,476
Patent document 38: U.S. Pat. No. 5,068,536
Patent document 39: U.S. Pat. No. 5,576,544
Patent document 40: U.S. Pat. No. 5,703,364
Patent document 41: U.S. Pat. No. 5,028,787
Patent document 42: U.S. Pat. No. 5,086,229
Patent document 43: U.S. Pat. No. 5,324,979
Patent document 44: U.S. Pat. No. 5,237,178
Patent document 45: U.S. Pat. No. 5,360,004
Patent document 46: U.S. Pat. No. 5,460,177
Patent document 47: U.S. Pat. No. 5,379,764
Patent document 48: U.S. Pat. No. 5,747,806
Patent document 49: U.S. Pat. No. 5,945,676
Patent document 50: U.S. Pat. No. 6,280,381
Patent document 51: U.S. Pat. No. 5,957,841
Patent document 52: U.S. Pat. No. 6,016,435
Patent document 53: U.S. Pat. No. 5,636,633
Patent document 54: U.S. Pat. No. 5,655,530
Patent document 55: U.S. Pat. No. 6,230,034
Patent document 56: U.S. Pat. No. 5,551,422
Patent document 57: U.S. Pat. No. 5,492,118
Patent document 58: U.S. Pat. No. 5,978,691
Non-Patent document 1: Amerov et al., "Molar absorptivities of glucose and other biological molecules in aqueous solutions over the first overtone and combination regions of the near-infrared spectrum", Applied Spectroscopy 58: 1195-1204 (2004)
Non-Patent document 2: Robinson et al., "Noninvasive glucose monitoring in diabetic patients: a preliminary evaluation", Clinical Chemistry 1992 September; 38(9): 1618-22

Non-Patent document 3: Maier et al., "Possible correlation between blood glucose concentration and the reduced scattering coefficient of tissues in the near infrared", Optics Letter 1994; 19: 2062-64

Non-Patent document 4: Kohl et al., "Influence of glucose concentration on light scattering in tissue stimulating phantoms", Optics Letters 1994; 19: 2170-72

Non-Patent document 5: Kohl et al., "The influence of glucose concentration upon the transport of light in tissue-stimulating phantoms", Physics Medicine Biology 1995; 40: 1267-87

Non-Patent document 6: Heinmann et al., Diabetes Technology Therapeutics 2000; 2: 211-220

Non-Patent document 7: Laufer et al., "Effect of temperature on the optical properties of ex vivo human dermis and subdermis", Phys. Med. Biol. (1998) volume 43: 2479-2489

Non-Patent document 8: Bruulsema et al., "Optical Properties of Phantoms and Tissue Measured in vivo from 0.9-1.3 μm using Spatially Resolved Diffuse Reflectance", SPIE Proceedings 2979 (1997) 325-334

Non-Patent document 9: Khalil et al., "Temperature modulation of the visible and near infrared absorption and scattering coefficients of intact human skin", J Biomedical Optics, 2003; 8: 191-205

Non-Patent document 10: Yeh et al., "Near Infrared Thermo-Optical Response of The Localized Reflectance of Intact Diabetic and Non-Diabetic Human Skin", J Biomedical Optics, 2003; 8: 534-544

Non-Patent document 11: Yeh et al., "Tracking Blood Glucose Changes in Cutaneous Tissue by Temperature-Modulated Localized Reflectance Measurements", Clinical Chemistry 2003; 49: 924-934

Non-Patent document 12: Khalil et al., "Response of near IR localized reflectance signals of intact diabetic human skin to thermal stimuli", SPIE Proceedings 2003; 5086: 142-148

Non-Patent document 13: Cho et al., "Noninvasive measurement of glucose by metabolic heat conformation method", Clinical Chemistry 2004; 50: 1984-1988

Non-Patent document 14: Ko et al., "Body metabolism provides a foundation for noninvasive blood glucose monitoring", Diabetes Care, 2004; 27: 1211-2

Non-Patent document 15: Malchoff et al., "A novel noninvasive blood glucose monitor", Diabetes Care 2002; 25: 2268-75

Non-Patent document 16: Heinemann et al., Diabetes Technology Therapeutics 2000; 2: 211-220

BRIEF SUMMARY OF THE INVENTION

An object of the present invention is to track temperature-induced glycolysis by inducing a temperature change in the human skin, measuring localized reflectance signals at several defined light source-detector distances, and correlating functions derived from the reflectance values obtained at a plurality of wavelengths and light source-detector distances with glucose concentrations in a method for noninvasive measurement of glucose and an apparatus for noninvasive measurement of glucose.

One aspect of the invention is a method for noninvasive measurement of glucose in a subject in which enhancement of the time dependence of glucose metabolism by glycolysis is induced, including the steps of: inducing a change in glucose metabolism in a nutrient capillary in the skin by bringing at least one localized reflectance optical probe whose temperature has been modulated to a temperature substantially different from the normal temperature of the skin such that a change in temperature of a tissue in the very vicinity of the probe and up to a depth surrounded by the skin vascular system is induced, and the temperature change causes a change in the rate of glycolysis, and the temperature-enhanced glycolysis causes a change with respect to light attenuation, oxygen consumption in a tissue and the concentration of a hemoglobin variant into contact with the skin; measuring a change in localized reflectance light signals at a plurality of light source-detector distances and a plurality of wavelengths as a function of a time for which the localized reflectance probe is brought into contact with the skin over a specific time window from the skin-probe contact; selecting a time window in which a tissue-probe adaptation effect on the signals is reduced to the minimum and the effect of glycolysis induced by the temperature has time dependence and using the signals measured in the time window for subsequent calculation; calculating one set of functions based on the plurality of localized reflectance values at the plurality of light source-detector distances and the plurality of wavelengths at a plurality of time intervals in the time window and at least two wavelengths; deriving a calibration relationship between a combination of the calculated functions and a glucose concentration in a living body; and using the calibration relationship for predicting a glucose concentration in a body fluid in a subsequent measurement.

Another object of the invention is to reduce the influence of mechanical and thermal effects occurring when the measurement probe is brought into contact with the skin of a subject.

Another aspect of the invention is an apparatus for noninvasive measurement, with which glucose in a subject is noninvasively measured optically through a measurement probe, including a light source and a light detector both of which are connected to the measurement probe, an adaptation device which has a shape similar to the measurement probe, and a computer unit which implements noninvasive measurement by controlling the light source and the light detector, and also ahead of the noninvasive measurement, controls the adaptation device such that the adaptation device is brought into contact with a skin part of a subject for stretching the skin part of the subject under a pressure that is higher than a pressure per unit area applied by the measurement probe during the noninvasive measurement.

DETAILED DESCRIPTION OF THE INVENTION

First Embodiment

Figure 1:
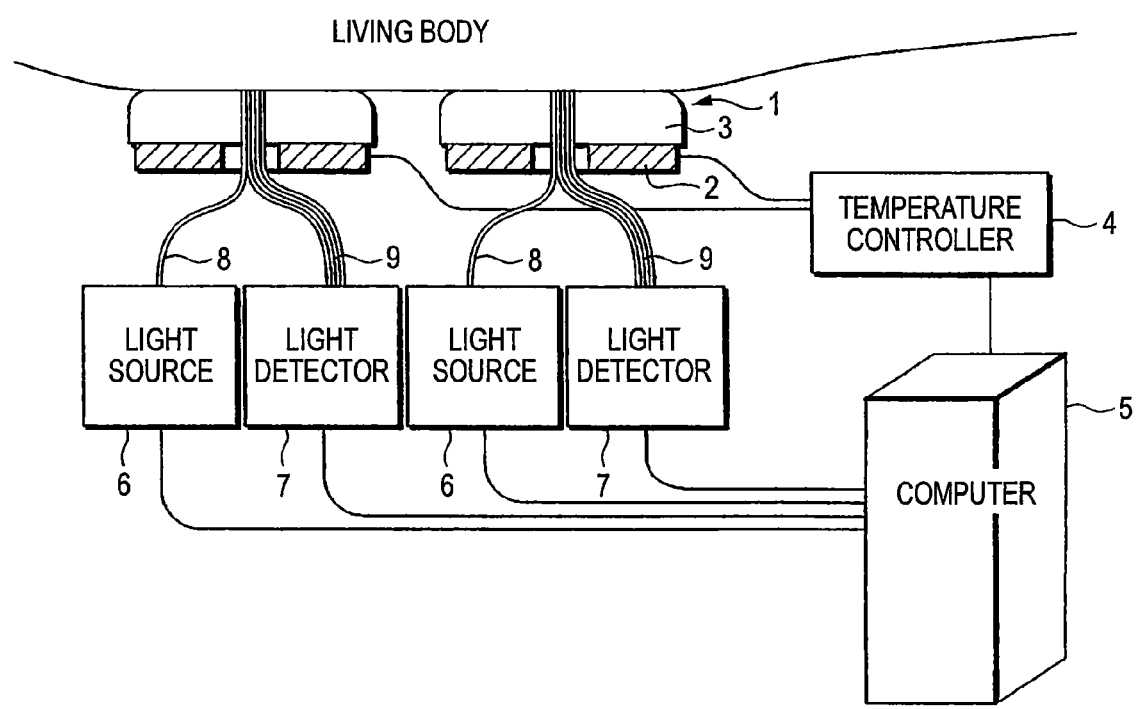
FIG. 1 is a diagram showing a configuration of an apparatus for noninvasive measurement of glucose according to a first embodiment.

A first embodiment of the present invention relates to a method for noninvasive measurement of glucose concentration in a subject. The method utilizes a property that transient glucose metabolism is affected by temperature and a light signal changes according to a change in the metabolism.

In the first embodiment of the invention, a temperature-modulated localized reflectance optical probe which is similar to a probe described in U.S. Pat. No. 6,662,030 by Khalil et al. and Khalil et al., J. Biomed. Opt. 2003; 8: 191-205, Yeh et al., J. Biomed. Opt. 2003; 8: 534-44, and Yeh et al., Clin. Chem. 2003; 49: 924-34 is used. In the measurement of localized reflectance signals using a temperature-modulated probe described in U.S. Pat. No. 6,662,030 (Khalil et al.), a light signal is generated according to a contact time between the probe at a temperature or a given temperature and a body part. The detected signal corresponds to light absorption by tissue chromophores and red blood cells, and light scattering from the center of tissue scattering and red blood cells. The visible and NIR light absorption by the blood mainly attributes to the light absorption by a hemoglobin variant in red blood cells (RBC). The variant includes oxyhemoglobin (about 95%) and deoxyhemoglobin (about 5%).

When a solid substance such as an optical probe comes into contact with the skin, several mechanical effects are caused. The probe presses the skin to cause local occlusion and further affects blood flow. In a similar manner, heat is transferred from the probe to the skin or vice versa depending on the thermal conductivity of a material of the probe and a difference in the temperature between the tissue and the probe. The adaptation of the soft skin to the rigid metal probe can appear as a time dependent change in measured light signal. The heat transfer to the skin induces a temporary temperature change at a measurement site. A subsequent temperature change in a nutrient capillary in the skin is caused followed by widening of a blood vessel and opening of capillary shunts. Most of the capillary shunts begin to open at 42° C. and completely open at 46° C.

Glucose is metabolized in human tissues in a continuous manner. A change in glucose metabolism has been used for detecting a tumor activity by injecting radioactive glucose into the vein of a patient and observing radioactive distribution in tissues by positron emission tomography (PET). Oxygen consumption in the brain has been calculated from NIR light signals for showing a cognitive activity. Oxygen consumption has been measured also in a tumor for detecting angiogenesis and excess metabolism in the tumor. Another method for measuring oxygen consumption is magnetic resonance of iron atoms in oxyhemoglobin and deoxyhemoglobin. This technique is called a functional magnetic resonance imaging method.

In glucose metabolism in a subject, there are three pathways, i.e., glycolysis, conversion into lipids, and glucose storage as glycogen. Glycolysis is oxidation of glucose into $CO_2$ and water, and takes place in all the living cells. Glucose conversion into lipids takes place in adipose tissues and muscle and liver cells. Glucose storage as glycogen takes place in liver cells.

In the first embodiment, the effect of temperature on glucose metabolism in the blood, particularly in red blood cells is employed. Red blood cells (also known as erythrocytes) cannot store glucose or use other substrates as an energy. Glycolysis is a major metabolic pathway of glucose in red blood cells. An oxygen source in red blood cells is oxygen transport protein hemoglobin. Transport of glucose (G) to red blood cells is instantaneous. Glucose is metabolized into carbon dioxide and water in RBC or remains there as a free glucose molecule. The free glucose in red blood cells causes glycosylation of hemoglobin to form glycosylated hemoglobin, HbA1c, which is a marker of poor blood glucose regulation. An increase in glucose concentration to a level exceeding a normal nondiabetic range leads to an increase in HbA1c concentration. A high HbA1c level is a sign of the onset of frequent hyperglycemia.

In the first embodiment, a temperature jump effect on a glycolysis process is used. In glycolysis in red blood cells, physically dissolved oxygen (smaller portion) or oxygen transported by hemoglobin, which is an oxygen transport protein, is consumed. An oxyhemoglobin molecule dissociates into deoxyhemoglobin and oxygen. A change in glucose metabolism leads to an instantaneous change in $HbO_2$ concentration. Subsequently, oxidized hemoglobin is supplied at a measurement site by breathing and blood flow. In the first embodiment of the invention, these effects are tracked by measuring the effects of temperature stimulation on localized reflectance signals at a plurality of wavelengths corresponding to light absorption by an oxidized hemoglobin variant.

In the first embodiment, the effect of temperature on glucose metabolism with respect to light scattering from the blood and a tissue component is used. A scattering coefficient in a tissue is determined by the refractive index mismatch between the center of tissue scattering and ISF. The refractive index $n_{ISF}$ of ISF is non-specific for glucose, but determined by a glucose concentration. U.S. Pat. Nos. 5,551,422 and 5,492,118 disclose the use of a scattering coefficient change for NI measurement of glucose. The subject experiment (Diabetes Technology and Therapeutics 2000; 2: 211-220) shows nonspecificity of the effect and lack of correlation with glucose. A change in glycolysis induces a change in refractive index as glucose molecules in the blood are consumed. By incorporating a change in scattering and absorption when changing the temperature, specificity of signals measured can be provided.

The first embodiment is a method for noninvasive measurement of glucose in a subject. The method includes bringing a localized reflectance optical probe whose temperature has been set to a temperature substantially different from the normal temperature of the human skin into contact with the skin for inducing a sudden temperature change in the skin tissue. A temperature-enhanced change in glucose metabolism (glycolysis) in red blood cells is caused, and oxygen is consumed. There is a temporary stoichiometric relationship between glucose and $HbO_2$ concentration. This relationship can be a source of signal specificity. The oxygen consumption in RBC can be calculated from light absorption by red blood cells at various wavelengths and various light source-detector distances.

According to the first embodiment, the localized reflectance probe whose temperature is substantially different from the normal temperature of a tissue is brought into contact with the human skin, whereby a change in glucose concentration associated with the ambient glucose concentration is induced. As a result of this perturbation, the glucose concentration can be expressed in terms of a physical parameter and a physiological parameter. The physical parameter is associated with a rate of change in effective attenuation coefficient according to the probe-skin contact time. Further, a change in blood flow, widening of a blood vessel and scattering by tissue and blood cells will be induced. The physiological parameter is associated with a rate of oxygen consumption according to the probe-skin contact time.

According to the first embodiment, a temperature higher than the normal temperature of the skin can cause enhanced glycolysis in a nutrient capillary before the capillary system reaches an equilibrium with ambient tissues by widening of a blood vessel.

According to the first embodiment, glycolysis in RBC is dependent on temperature. The rate of glycolysis changes as a temperature changes in a range from 30 to 42° C. The rate is constant at a body core temperature of 37° C. A skin temperature is lower than the body core temperature. A sudden increase in temperature in a short time of about 60 sec can cause a change in the consumption of oxygen in a capillary and a rate of glycolysis before oxygen is supplied by blood flow and normal breathing.

According to the first embodiment, a blood glucose concentration affects a rate of glycolysis in a nutrient capillary and the response to the thermal stimulation. The rate of glycolysis is determined by an initial glucose concentration in red blood cells and therefore by a blood glucose concentration. The degree of glycolysis over a defined time from the initiation of temperature-induced glycolysis is determined by an initial glucose concentration in red blood cells and therefore by a blood glucose concentration. When quasi-one dimensional rate is used, the rate of glycolysis can be represented as follows.

$$d[G]/dt = -k_1[G]_{RBC} \quad (1)$$

$$[G]_{RBC} = \chi[G]_{Blood} \quad (2)$$

($\chi$ represents a partition coefficient which is a fractional number determined by the diabetic conditions, insulin concentration and insulin sensitivity of a human.)

In another aspect of the first embodiment, a rate of change in glycolysis is associated with a rate of oxygen consumption in red blood cells, and can be measured at least two wavelengths, and the at least two wavelengths have values substantially different with respect to the extinction coefficient of deoxyhemoglobin and that of oxyhemoglobin. Oxygen consumption in RBC is calculated according to a time from the initiation of contact of the skin with the measurement probe having a temperature substantially different from an ambient skin temperature.

$$d[G]/dt \approx -k_2 d[HbO_2]/dt = k_3 d[\text{oxygen consumption}]/dt \quad (3)$$

and $$d[G]/dt \approx k_4 d\mu_{\text{eff}}/dt \quad (4)$$

A glucose concentration can be represented as follows based on the assumption of one-dimensional kinetics.

$$[G] \approx k_4 d[\text{oxygen consumption}]/dt \quad (5)$$

and $$[G] \approx k_5 d\mu_{\text{eff}}/dt \quad (6)$$

According to the first embodiment, a glucose concentration can be calculated from the sum of two responses as follows.

$$[G] = \Sigma_i [f_{1i}(\text{physical response})] + \Sigma_j [f_{2j} (\text{physiological response})] \quad (7)$$

In another aspect of the first embodiment, a change in relative reflectance at two wavelengths corresponding to light absorption by a hemoglobin variant is caused as a result of thermal stimulation applied to a nutrient capillary. This change in absorption by hemoglobin in the capillary bed is used as an index of the degree of glucose metabolism or the rate of glycolysis in red blood cells. Glycolysis is the only metabolic pathway of glucose in red blood cells, therefore, a change in oxidized state of hemoglobin is an index specific for glycolysis and can be used as an index of a blood glucose concentration. The rate of oxygen consumption and the degree of oxygen consumption can be used as a physiological parameter and also can have a correlation with a change in glucose concentration.

U.S. Pat. No. 6,662,030 describes a temperature-modulated localized reflectance probe which can be used in the method of the first embodiment. The temperature-modulated probe has a light introduction fiber and several light collection fibers. The light collection fibers are disposed at a short distance from the light introduction fiber. The maximum light source-detector distance is a center-center distance of less than 2 mm between the center of the light introduction fiber and the light collection fiber. By selecting the light source-detector distance of less than 2 mm, measurement of light signals generated from the upper skin layer without entrapping signals from adipose tissues or muscle tissues is surely carried out.

One aspect of the first embodiment is the use of a localized reflectance probe whose temperature has been set to a temperature substantially different from the normal temperature of the skin for collecting thermooptical response signals. The temperature of the probe is maintained at a temperature substantially different from the normal temperature of the skin. A sudden temperature change upon contacting of the skin with the probe induces a change in glucose metabolism in a nutrient capillary in the skin.

In still another aspect of the first embodiment, a glucose concentration is associated with a rate of change in effective attenuation coefficient according to a probe-skin contact time and a rate of oxygen consumption according to a probe-skin contact time. Accordingly, we represent the equation 7 as follows.

$$[G] = \Sigma_i [a_i^* \{(d\mu_{eff}/dt)\}\lambda_i] + \Sigma_j [b_j^* (dOC/dt) r_j] \quad (8)$$

The sum of the first term ranges over a plurality of wavelengths ($\lambda_i$) used, and the sum of the second term ranges over numerical values ($r_j$) of the light source-detector distances used in the localized reflectance measurement. The term $\mu_{eff}$ is an effective attenuation coefficient, which is associated with an absorption coefficient of a medium: $\mu_a = 2303\epsilon C$ and a scattering coefficient of a medium: $\mu'_s$ by the relational formula: $\mu_{eff} = [(3\mu_a(\mu_a + \mu'_s))]^{1/2}$.

The rate of change in oxygen consumption can be represented as a ratio of $\mu_a$ at a wavelength at which absorption of deoxyhemoglobin is higher than that of oxyhemoglobin to $\mu_a$ at a wavelength at which absorption of deoxyhemoglobin is lower than that of oxyhemoglobin. Table 1 shows $\epsilon$ of oxyhemoglobin and deoxyhemoglobin, and calculated $\mu_a$ values of two types of hemoglobin, the total hemoglobin at an oxygen saturation value of 95% and a total hemoglobin of 15 g/dL. Selected wavelengths were used in an apparatus for testing the first embodiment, and a large difference in $\epsilon$ between two hemoglobin types is shown. Several wavelengths among these are shown in Table 1, and $\epsilon$ and $\mu_a$ of oxyhemoglobin and deoxyhemoglobin and the total hemoglobin are calculated with respect to a total hemoglobin concentration of 15 g/dL and an oxygen saturation value of 95% in Table 1.

TABLE 1

Extinction coefficient and absorption coefficient of hemoglobin

| Wavelength | Total Hb (15 g/dL) | Oxyhemoglobin | | Deoxyhemoglobin | |
| --- | --- | --- | --- | --- | --- |
| nm | $\mu_a$ (cm$^{-1}$) | $\epsilon$ | $\mu_a$ (cm$^{-1}$) | $\epsilon$ | $\mu_a$ (cm$^{-1}$) |
| 592 | 24.35 | 10468 | 21.59 | 25470 | 2.76 |
| 660 | 1.01 | 320 | 0.66 | 3227 | 0.35 |
| 880 | 2.58 | 1214 | 2.5 | 736 | 0.08 |
| 940 | 2.58 | 1214 | 2.5 | 693 | 0.08 |

When a pair of wavelengths in Table 1 is used, a rough estimate of a rate of change in oxygen consumption can be represented as follows.

$$d(OC)/dt = \alpha \{d(\mu_a 660/\mu_a 940/dt)\} \quad (9a)$$

$$d(OC)/dt = \beta \{d(\mu_a 660/\mu_a 880/dt)\} \quad (9b)$$

The latter functional form is similar to one to be used in the calculation of arterial oxygen saturation in heart beating, which is known as pulse oximetry.

Approximate formulae for scattering and absorption terms

The plotting of $Ln(1/R(r_1))$ against $Ln(R(r_i)/R(r_1))$ provides tracking of the interaction between an absorption coefficient and a scattering coefficient using a Monte Carlo grid. The plotting of $Ln(1/R(r_1))$ against $Ln(R(r_i)/R(r_1))$ at various time points in the probe/skin interaction provides a Monte Carlo-like grid, and its slope can be associated with an effective attenuation coefficient $\mu_{eff}$.

It is possible to roughly calculate a change in scattering coefficient and absorption coefficient with respect to a localized reflected light intensity ratio at a defined light source-detector distance and wavelength. A change in physical response can be expressed as follows.

$$\Sigma_i [a_i^* \{(d\mu_{eff}/dt)\}\lambda_i] = \Sigma i [a_i^* \{dln(1/R_1)/dLn(R_i/R_1)\}\lambda_i] \quad (10)$$

A change in physiological response can be expressed as follows.

$$\Sigma_j [b_j^* \{d(\mu_a 660/\mu_a 940/dt)\}] = \Sigma_j [b_j^* \{dLn(R_{660}/R_{940})/dt\} r_j] \quad (11)$$

Accordingly, a blood glucose concentration can be expressed as follows with respect to a localized reflected light intensity ratio at a defined light source-detector distance and wavelength.

$$[G] = \Sigma_i [a_i^* \{dln(1/R_1)/dLn(R_i/R_1)\}\lambda_i] + \Sigma_j [b_j^* \{dLn(R_{660}/R_{940})/dt\} r_j] \quad (12)$$

Here, $\lambda_i$ is 592, 660 or 880 nm, and $r_j$ is a light source-detector distance. When the respective localization-reflectance signals are normalized to the initial time $t_0$ sec in the same time window between $t_n$ sec and t sec, the result is as follows.

$$[G] = \Sigma_i [a_i^* \{dln(1/R_1)/dLn(R_i/R_1)\}\lambda_i] + \Sigma_j [b_j^* \{Ln(R_{660}/R_{940})t/Ln(R_{660}/R_{940})t_0\} r_j] \quad (13)$$

The first term in the equation (13) describes a change in both absorption and scattering coefficients. The scattering is dominant in the shortest light source-detector distance and a low absorption value. The absorption is dominant in the longest light source-detector distance and a high absorption value. This shall apply to the measurement at a hemoglobin absorption wavelength.

The metabolic effect of temperature on oxygen consumption will be described.

Another calculation for the method of the first embodiment in which $\epsilon$ values of oxyhemoglobin and deoxyhemoglobin are used for deriving coefficients of oxygen consumption equation. The derived equation shows an association between a localized reflected light intensity at a defined light source-detector distance and wavelength and a ratio of a hemoglobin $\epsilon$ value to a change in glucose concentration. We will start from the formula of $\mu_a$ of the blood at a wavelength used in a measurement apparatus.

$$(\mu_a)_{592\,nm} \text{ at start} \approx Ln(R_{592})_0 = \epsilon C[HbO2(0)] + \epsilon C[Hb(0)], \text{ at 592 nm} \quad (14)$$

$$(\mu_a)_{592\,nm} \text{ at t sec} \approx Ln(R_{592})_t = \epsilon C[HbO2(t)] + \epsilon C[Hb(t)], \text{ at 592 nm} \quad (15)$$

$$(\mu_a)_{592\,nm} \text{ at start} \approx Ln(R_{592})_0 = 10,468*C[HbO2(0)] + 25,470*[Hb(0)] \quad (16)$$

$$(\mu_a)_{592\,nm} \text{ at t sec} \approx Ln(R_{592})_t = 10,468*C[HbO2(t)] + 25,470*[Hb(t)] \quad (17)$$

A similar equation can be written for other wavelengths of 660, 880 and 940 nm. By subtracting the equation (16) from the equation (17), a change in the absorption coefficient at 592 nm is shown as follows as a result of temperature jump.

$$\Delta(\mu_a)_{592\,nm} \approx Ln[(R_{592})_t/(R_{592})_0] = 10,468*\Delta C[HbO2] + 25,470*\Delta C[Hb] \quad (18)$$

$\Delta C[HbO2]$ is a change in $HbO_2$ concentration induced by temperature, which generates oxygen necessary for temperature-induced glycolysis. A similar equation is applies to other wavelengths, and the equations (19) to (21) are provided.

$$\Delta(\mu_a)_{660\,nm} \approx \text{Ln}[(R_{660})_t/(R_{660})_0] = 320*C[HbO2] + 3{,}227*C[Hb] \quad (19)$$

$$\Delta(\mu_a)_{880\,nm} \approx \text{Ln}[(R_{880})_t/(R_{880})_0] = 1{,}214*C[HbO2] + 673*C[Hb] \quad (20)$$

$$\Delta(\mu_a)_{940\,nm} \approx \text{Ln}[(R_{940})_t/(R_{940})_0] = 1{,}214*C[HbO2] + 6{,}934*C[Hb] \quad (21)$$

By multiplying the equation (21) by 36.75, the equations (18) and (21) are solved with respect to C[HbO$_2$], and the equation (22) is provided.

$$36.75*\text{Ln}[(R_{940})_t/(R_{940})_0] = 36.75 \times 1{,}214*C[HbO2] + 25{,}470*C[Hb] \quad (22)$$

The equation (22) is subtracted from the equation (18).

$$\{36.75*\text{Ln}[(R_{940})_t/(R_{940})_0] - \text{Ln}[(R_{592})_t/(R_{592})_0]\} = 34{,}150*\Delta C[HbO2] \quad (23)$$

The equation is solved with respect to $\Delta C[HbO_2]$.

$$\Delta C[HbO2] = (2.928 \times 10^{-5})*\{36.75*\text{Ln}[(R_{940})_t/(R_{940})_0] - \text{Ln}[(R_{592})_t/(R_{592})_0]\} \quad (24)$$

By solving the equation with respect to 880 nm and 592 nm, the following equation is provided.

$$\Delta C[HbO2] = (2.928 \times 10^{-5})*\{36.75*\text{Ln}[(R_{880})_t/(R_{880})_0] - \text{Ln}[(R_{592})_t/(R_{592})_0]\} \quad (25)$$

In the embodiment of the first embodiment, a change in the molar concentration of glucose by excess glycolysis, $\Delta[G]$, is associated with $\Delta C[HbO2]$.

$$\Delta[G] \alpha 2.928 \times 10^{-5}*\{36.75*\text{Ln}[[(R_{940})_t/(R_{940})_0] - \text{Ln}[(R_{592})_t/(R_{592})_0]] \quad (26)$$

In order to convert $\Delta[G]$ from a mole unit to mg/dl, it is multiplied by $1.8 \times 10^4$.

$$\Delta[G]/\alpha\Delta C[HbO_2]/\alpha F(OC)_1 = 0.527*\{36.75*\text{Ln}[[(R_{940})_t/(R_{940})_0] - \text{Ln}[(R_{592})_t/(R_{592})_0]] \quad (27)$$

$F(OC)_1$ is a function representing oxygen consumption from localization-reflectance optical measurement at 592 nm and 940 nm.

According to the following same steps, it is possible to calculate the oxygen consumption function, $F(OC)_2$, from the reflectances measured at 660 nm and 940 nm.

By multiplying the equation (21) by 4.6566, the equations (19) and (21) are solved with respect to $\Delta C[HbO2]$, and the equation (28) is provided.

$$4.6566*\text{Ln}[(R_{940})_t/(R_{940})_0] = 5{,}653*\Delta C[HbO2] + 3{,}227*C[Hb] \quad (28)$$

The equation (19) is subtracted from the equation (28).

$$\{4.969*\text{Ln}[(R_{940})_t/(R_{940})_0] - \text{Ln}[(R_{660})_t/(R_{660})_0]\} 5{,}621*\Delta C[HbO2] \quad (29)$$

$$\Delta C[HbO2] = (1/5621)*\{4.6566*\text{Ln}(R_{940})_t/(R_{940})_0 - \text{Ln}[(R_{660})_t/(R_{660})_0]\} \quad (30)$$

$$\Delta C[HbO2] = 1.779 \times 10^{-14}*\{4.6566*\text{Ln}[(R_{940})_t/(R_{940})_0] - \text{Ln}[(R_{660})_t/(R_{660})_0]\} \quad (31)$$

In the embodiment of the invention, $\Delta C[HbO2]$ has a correlation with $\Delta[glucose]$, $\Delta[G]$, and a change in the molar concentration of glucose by excess glycolysis caused as a result of thermal stimulation is proportional to $\Delta C[HbO2]$ in the same manner as the case of the equation (26).

$$\Delta[G] \alpha 1.779 \times 10^{-4}*\{4.6566*\text{Ln}[(R_{940})_t/(R_{940})_0] - \text{Ln}[(R_{660})_t/(R_{660})_0]\} \quad (32)$$

In order to convert the concentration of $\Delta[G]$ from a mole unit to mg/dl, it is multiplied by $1.8 \times 10^4$.

$$\Delta[G]/\alpha\Delta C[HbO_2]/\alpha F(OC)_2 = 3.2022*\{4.6566*\text{Ln}[(R_{940})_t/(R_{940})_0] - \text{Ln}[(R_{660})_t/(R_{660})_0]\} \quad (33)$$

$F(OC)_2$ is a function representing oxygen consumption from localization-reflectance optical measurement at 660 nm and 940 nm. The oxygen consumption functions, $F(OC)_1$ and $F(OC)_2$, are conceptually similar to each other, but can have different values depending on a skin structural effect.

An equation obtained by generalizing the equations representing a glucose concentration with respect to a change in all the attenuation coefficients and oxygen consumption functions is as follows.

$$[G] = a_0 + \Sigma_i [a_i*\{dln(1/R_1)/dLn(R_i/R_1)\}\lambda_i] + \Sigma_j [b_j*\{F(OC)_1\}r_j] + \Sigma_k [b_k*\{F(OC)\}r_k] \quad (34)$$

Various modifications of this equation and various determination criteria for the range of variables in the equation can be used.

Time Window for Calculation

The calculation method of this embodiment includes the step of calculating a rate of change in localized reflectance values at a plurality of wavelengths and light source-detector distances. In a modification example of the first embodiment, the calculation method includes the step of calculating a degree of change in at least one parameter associated with the time dependent effect of the temperature stimulation on the localized reflectance values at a plurality of wavelengths and light source-detector distances. The degree of change is calculated for at least one time window and is averaged over adjacent time windows. The time window for calculation starts after the skin-probe adaptation.

Advantage of this Embodiment

This embodiment is different from the prior art in several aspects. In the first embodiment, temperature-induced glycolysis is tracked by inducing a temperature change in the human skin, measuring localized reflectance signals at several defined light source-detector distances, and correlating functions derived from the reflectance values at a plurality of wavelengths and light source-detector distances with a glucose concentration.

U.S. Pat. Nos. 5,795,305 and 5,924,996, US Patent Application Publication No. 2005/0124868 and European Patent Application Publication No. 1537822 did not take the skin-probe adaptation effect on the optical and thermal signals into consideration, and did not induce a temperature change that affects glucose metabolism. U.S. Pat. No. 5,978,691 does not disclose the measurement of oxygen consumption as a result of the physiological effect of glucose metabolism or the use of temperature-enhanced glucose metabolism, or does not take the time window for reducing the tissue-probe adaptation effect on the measurement to the minimum into consideration. In U.S. Pat. No. 5,978,691, a temperature-induced change in the hemoglobin equilibrium is measured. The method includes measurement of diffuse reflectance or transmission. This does not specify a defined light source-detector distance, and thus does not specify a depth in a tissue.

In the method and apparatus of this embodiment, a time for adaptation of the skin to the measurement probe is set, and signals to be measured over a specific time window, in which the skin-probe interaction effect on the signals is reduced to the minimum are used. U.S. Pat. No. 5,785,305, U.S. Pat. No. 5,924,996 and U.S. Pat. No. 5,978,691 do not set a time for adaptation of the measurement probe to the skin or do not use signals to be measured over a specific time window, in which the skin-probe adaptation effect on the signals is reduced to the minimum.

The main feature of this embodiment is as follows:

a. the step of measuring a change in localized reflectance according to time at a wavelength corresponding to light absorption by oxyhemoglobin and deoxyhemoglobin and calculating functions associated with a change in oxygen consumption;

b. the step of selecting a time window in which a tissue-probe adaptation effect on a signal is reduced to the minimum; and c. the step of deriving a calibration relationship between a combination of these oxygen consumption functions and a glucose concentration, and using the resulting calibration relationship for predicting a glucose concentration in the body are included.

Figure 2:
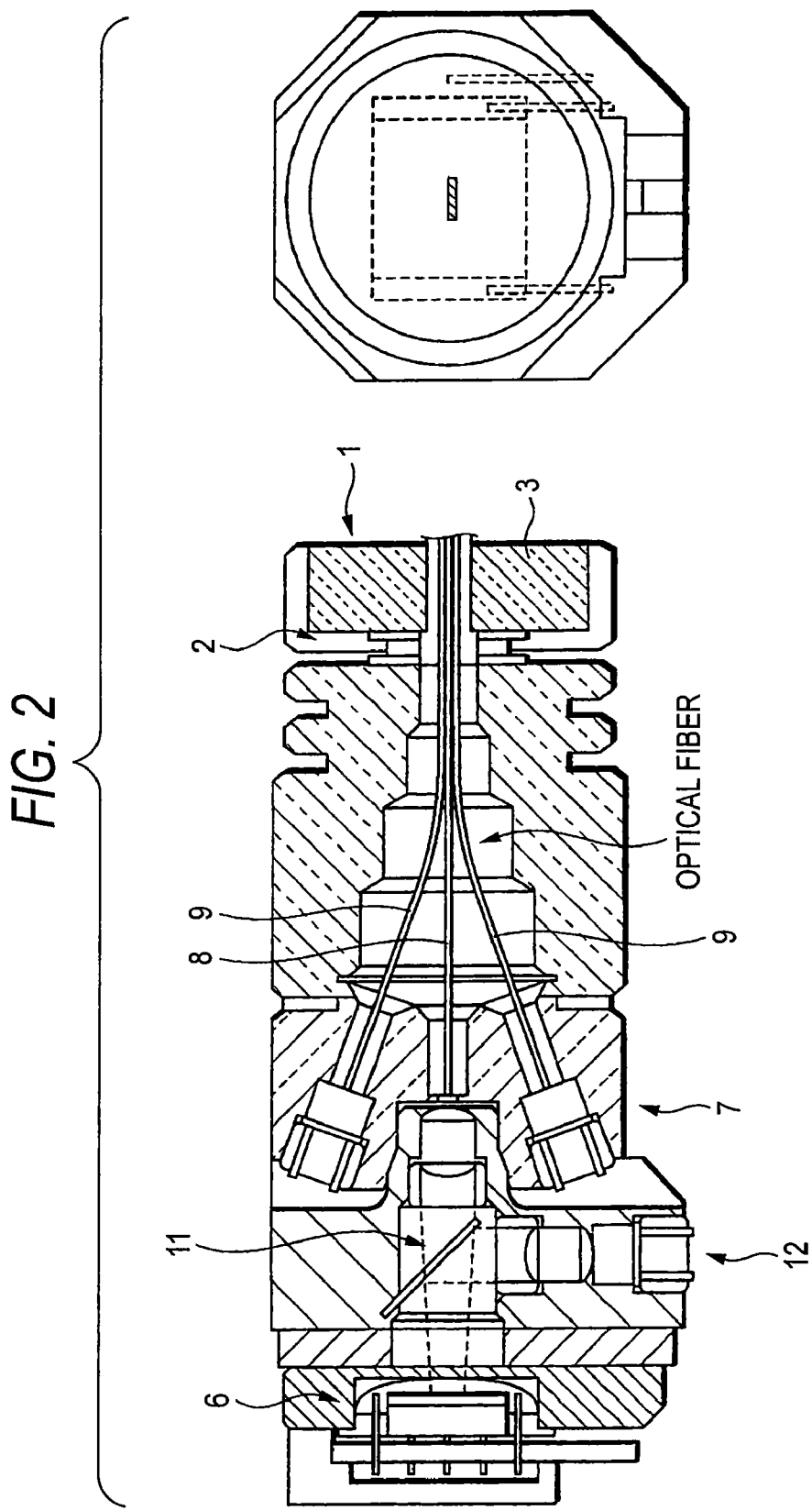
FIG. 2 is a diagram showing a structure of a read head of the apparatus for noninvasive measurement of FIG. 1.

FIG. 1 shows an apparatus for noninvasive measurement of glucose according to this embodiment. FIG. 2 shows a specific structure of a measurement head (also referred to as a probe) of the apparatus for noninvasive measurement of glucose of FIG. 1. A temperature control pack 1 includes a thermoelectric module 2 as a heat generator and a pad 3 which is contacted with the skin of a subject. The heating value of the thermoelectric module 2 is modulated by a temperature controller 4. Further, the temperature modulation operation of the temperature controller 4 is under the control of a computer 5. The computer 5 controls the temperature modulation and also plays a role in controlling the operating procedure of the method for noninvasive measurement of glucose according to this embodiment and operating the respective steps. In a central portion of the control pack 1, a tubular opening is formed and optical fibers 8 and 9 are inserted therein. To the optical fiber 8, a light source 6 is optically connected, and to the optical fibers 9, a light detector (signal detector) 7 is optically connected. Between the light source 6 and the optical fiber 8, a beam splitter 11 is disposed, and a part of light from the light source 6 is introduced into a reference detector 12.

The optical fiber 8 is disposed in the center, and the optical fibers 9 are arranged around the optical fiber 8 at short intervals. The maximum distance between the optical fiber 8 and the optical fibers 9 is less than 2 mm. That is, the optical fibers 8 and 9 are bundled within an area in a substantially circular shape with a diameter of 4 mm. A relationship between the wavelength of the localized reflectance probe and the distance between the light source 6 and the detector 7 is shown in Table 2. As described in U.S. Pat. No. 6,654,620, one drop of silicone oil is applied to the skin of a subject and then wiped off to leave a very thin layer of oil on the skin, whereby the thermal conductivity is enhanced.

TABLE 2

Wavelength and source-detector distance

| Wavelength nm | | Source-detector distance mm | |
|---|---|---|---|
| $\lambda_1$ | 592 | $r_1$ | 0.559 |
| $\lambda_2$ | 660 | $r_2$ | 0.879 |
| $\lambda_3$ | 880 | $r_3$ | 1.318 |
| $\lambda_4$ | 940 | $r_4$ | 1.758 |

Calculation of Oxygen Consumption and Change in Attenuation Coefficient

Figure 3:
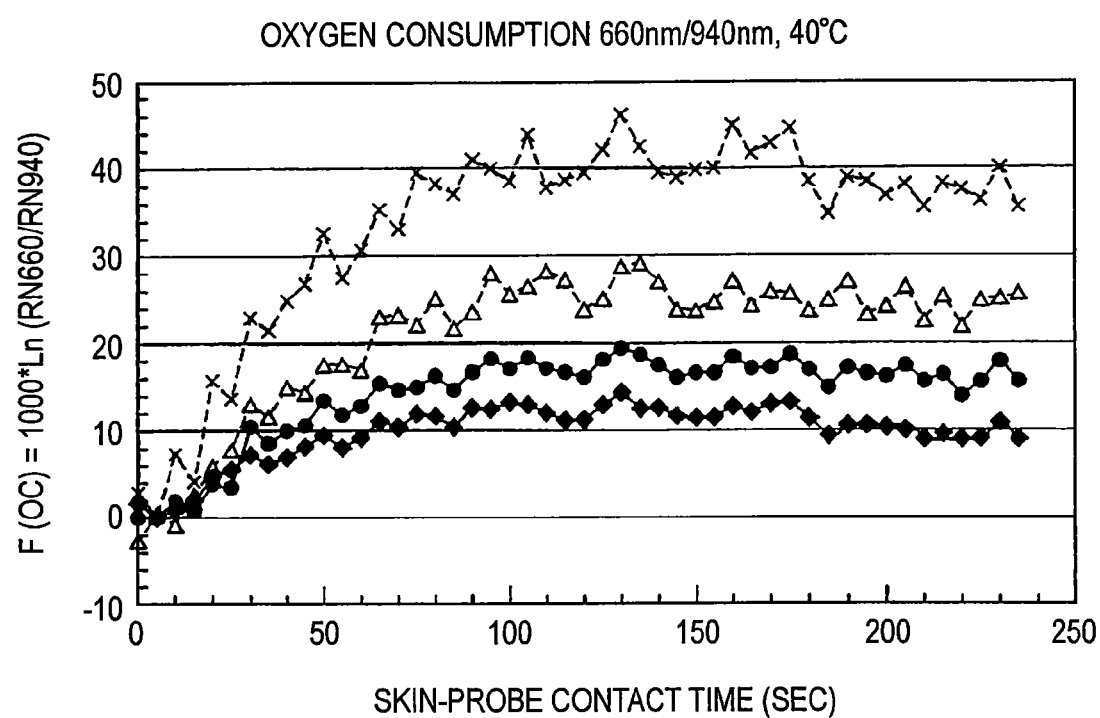
FIG. 3 shows functions of oxygen consumption obtained by using a probe at 40° C. with respect to various light source-detector distances. Lozenges indicate 0.559 mm, circles indicate 0.879 mm, triangles indicate 1.318 mm, and Xs indicate 1.758 mm.

FIG. 3 shows the response of the skin of a diabetic patient to an optical probe at 40° C. pressed against the skin of the forearm of the subject. The functions of oxygen consumption are calculated as follows using modification of the equation 9.

$$d(OC)/dt=\gamma*F(OC)=1000*Ln(R_{660}/R_{940})_t/Ln(R_{660}/R_{940})_5 \text{ sec} \quad (9c)$$

In the equation, R represents a localized reflectance at each light source-detector distance. The signals were normalized to signals at 5 sec intervals.

The calculated F(OC) increases when the probe at 40° C. is brought into contact with the skin, and then, reaches an asymptotic value after about 120 sec. The thermal modeling (J. Biomedical Optics., 2003; 8, 191-205) shows that when the probe came into contact with the skin, the temperature up to a depth of 2 mm reached an equilibrium after 120 sec. F(OC) increases at all the light source-detector distances. The order of the increase in F(OC) is as follows.

$$F(OC)r_4>F(OC)r_3>F(OC)r_2>F(OC)r_1$$

Figure 4:
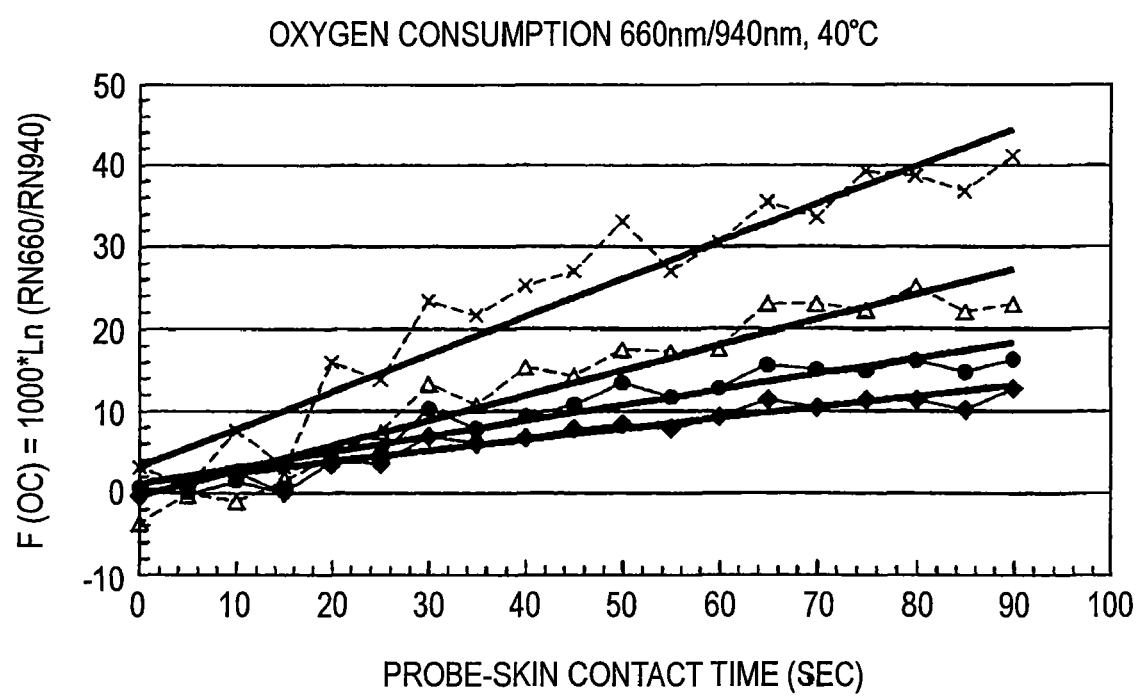
FIG. 4 shows F(OC) obtained by using a probe at 40° C. The time window was between 0 and 90 sec. Data was normalized to 5 sec data point. Lozenges indicate 0.559 mm, circles indicate 0.879 mm, triangles indicate 1.318 mm, and Xs indicate 1.758 mm. The lines are linear least squares approximation lines.

The maximum change in F(OC) occurs at initial 90 sec. As shown in FIG. 4, F(OC) value has a linear relationship with the skin-probe contact time.

Table 3 shows the results of calculation of functions of oxygen consumption at various light source-detector distances from the data of FIG. 4.

TABLE 3

Calculation of functions of oxygen consumption at various distances

| | Probe at 40° C. | |
|---|---|---|
| Source-detector distance mm | Fitting equation | Correlation coefficient ($r^2$) |
| 0.559 | F(OC) = 0.1363 t(s) + 1.0477 | 0.91 |
| 0.879 | F(OC) = 0.1925 t(s) + 1.0512 | 0.91 |
| 1.318 | F(OC) = 0.3114 t(s) + 0.5772 | 0.93 |
| 1.758 | F(OC) = 0.4498 t(s) + 3.7338 | 0.92 |

As shown in Table 3, the calculated functions of oxygen consumption linearly change with the time of probe-skin interaction at four light source-detector distances over the measured time window.

A rough estimate of a rate of change in effective attenuation coefficient at each wavelength according to the probe-skin contact can be achieved by plotting the values of $Ln(R_4/R_1)$ at the respective wavelengths against time and calculating the slope.

Figure 5:
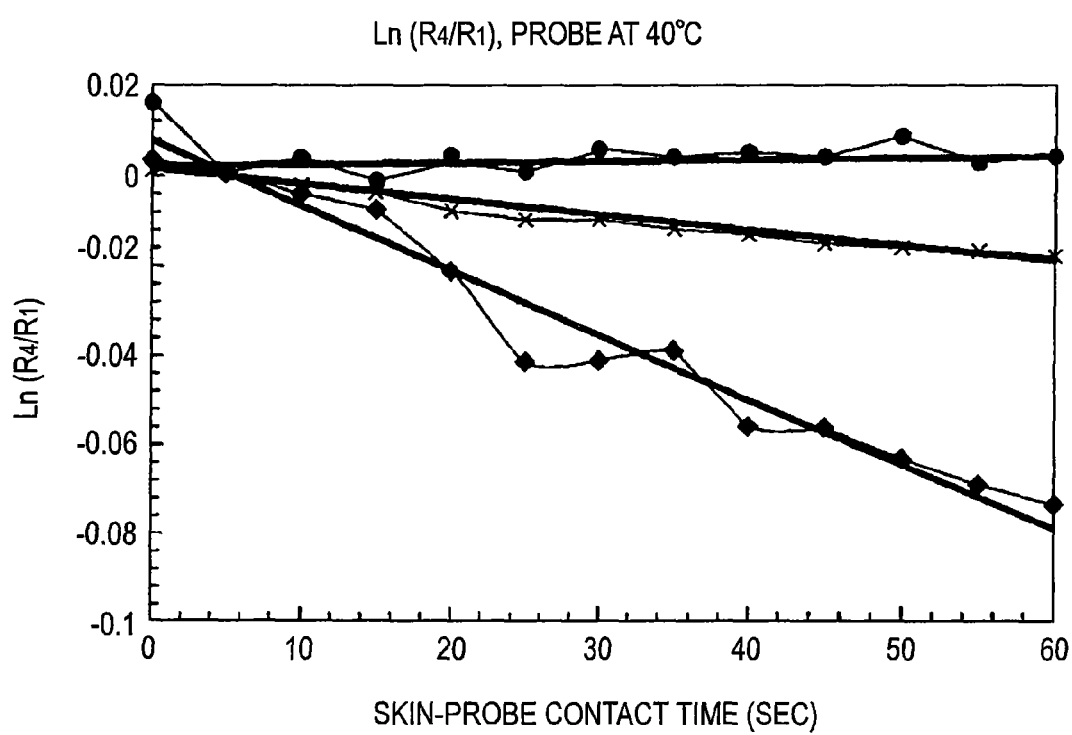
FIG. 5 shows a plot of $Ln(R_4/R_1)$ against time with respect to a probe heated to 40° C. Lozenges indicate 592 nm, circles indicate 660 nm, Xs indicate 880 nm, and triangles indicate 940 nm.

FIG. 5 shows the plot of $Ln(R_4/R_1)$ against time with respect to a probe heated to 40° C. Lozenges indicate 592 nm, circles indicate 660 nm, Xs indicate 880 nm, and triangles indicate 940 nm. Table 4 shows the results of calculation of approximate $\mu_{eff}$ represented by $Ln(R_4/R_1)$ and calculated at various wavelengths from the data of FIG. 5.

TABLE 4

Approximate $\mu_{eff}$ at various wavelengths

| | Probe at 40° C. | |
|---|---|---|
| Wavelength nm | Fitting equation | Correlation coefficient ($r^2$) |
| 592 | $Ln(R_4/R_1) = -1.5 \times 10^{-3} t(s) + 0.0088$ | 0.96 |
| 660 | $Ln(R_4/R_1) = +5.0 \times 10^{-5} t(s) + 0.0021$ | 0.15 |
| 880 | $Ln(R_4/R_1) = -0.3 \times 10^{-3} t(s) + 0.0013$ | 0.98 |
| 940 | $Ln(R_4/R_1) = -0.3 \times 10^{-3} t(s) + 0.0013$ | 0.98 |

The approximate $\mu_{eff}$ represented by $Ln(R_4/R_1)$ and calculated at various wavelengths changes linearly with the contact time in a time window between 5 and 90 sec except for the wavelength of 600 nm showing the smallest slope and low $r^2$. The slope approximates to $\mu_{eff}$ and changes in the following order.

$$Ln(R_4/R_1)_{592\,nm} > Ln(R_4/R_1)_{880\,nm} = Ln(R_4/R_1)_{940\,nm} \gg Ln(R_4/R_1)_{660\,nm}$$

A change in the slope is similar to a change in the extinction coefficient reported at various wavelengths, $\epsilon(HbO_2)$ or $\mu_a(HbO_2)$, however, 660 nm which provides the smallest value of $\epsilon(HbO_2)$ is excluded. This shows that a change in light absorption is the dominant contributor to be reflected light intensity.

Degree of Signal Change and Use of Moving Average of Signal Change

Figure 6:
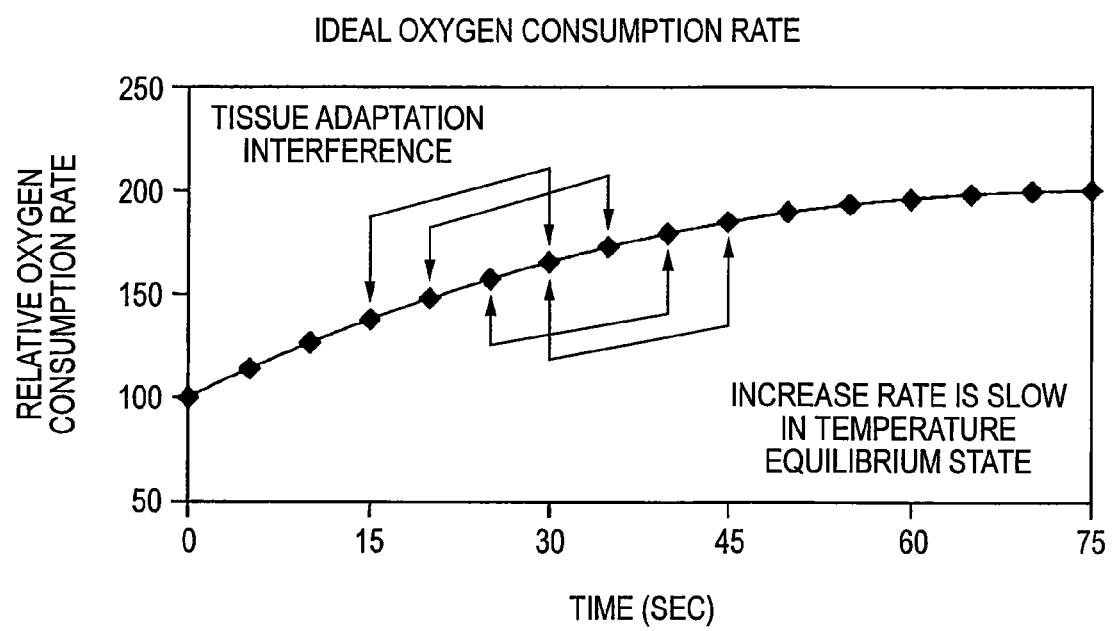
FIG. 6 shows simulation of profile of change in oxygen consumption rate when the skin is brought into contact with a probe heated such that the temperature thereof is increased by about 10° C.

The degree of change F(OC) is averaged over several adjacent time regions by using a moving average calculation. FIG. 6 shows simulation of profile of change in oxygen consumption rate when the skin is contacted with a probe heated such that the temperature thereof is increased by about 10° C. The 4-point moving average regions include data between 15 and 30 sec, time regions between 20 and 35 sec, 25 and 40 sec, and 30 and 45 sec. These time regions are used when the data of an embodiment 8 is analyzed.

Blood Glucose Concentration and Clinical Correlation

A clinical study was carried out in a hospital for diabetic patients who accepted treatment and signed informed consent. The ethical committee approved the study procedure. The testing time lasted 3 to 5 days. Each patient performed the test several times a day by using a NI apparatus and a home glucometer. The patients maintained daily activities and a therapeutic regimen. The data of 6 patients analyzed by using the modification of the equation 34 are shown in Table 5, however, in Table 5, an inclusion standard for data points in the subsequent calculation is included. The inclusion standard was as follows. a) d(OC)/dt<0, b) dLn($R_{592}$)/dt<0, c) dLn($R_{880}$)/dt<0 calibration points and prediction points were plotted on a Clarke Error Grid scatter diagram using a modification of the equation 34. The Clarke Error Grid is commonly used for showing the distribution of predicted glucose values in various zones of plots, and the respective zones of plots have a special clinical significance in predicted intervention.

TABLE 6

Data analysis of 6 diabetic patients using equations 34a to 34n, time interval between 5 and 60 sec, and a probe at 40° C.

| Equation No. | Number of terms | Type of term: constant + | n | $r_c$ | SEC mg/dl | $r_p$ | SEP mg/dl |
|---|---|---|---|---|---|---|---|
| 34a | 5 | 2 $\mu_{eff}$ + 2 OC | 39 | 0.81 | 45.4 | 0.44 | 123.0 |
| 34b | 5 | 2 $\mu_{eff}$ + 2 OC | 39 | 0.81 | 44.5 | 0.24 | 118.4 |
| 34c | 5 | 2 $\mu_{eff}$ + 2 OC | 42 | 0.81 | 44.3 | 0.28 | 146.4 |
| 34d | 2 | $\mu_{eff}$ | 43 | 0.74 | 50.4 | 0.73 | 60.3 |
| 34e | 2 | $\mu_{eff}$ | 40 | 0.7 | 53.7 | 0.71 | 64 |
| 34f | 2 | $\mu_{eff}$ | 43 | 0.7 | 49.7 | 0.72 | 62.4 |
| 34g | 3 | 2 $\mu_{eff}$ | 40 | 0.75 | 49.7 | 0.72 | 62.4 |
| 34h | 3 | 2 $\mu_{eff}$ | 43 | 0.75 | 49.4 | 0.72 | 61.6 |
| 34i | 2 | OC | 41 | 0.74 | 51.2 | 0.74 | 60.4 |
| 34j | 2 | OC | 42 | 0.74 | 50.5 | 0.72 | 61.7 |
| 34k | 3 | 2 OC | 42 | 0.76 | 49.3 | 0.72 | 62.8 |
| 34l | 4 | $\mu_{eff}$ + 2 OC | 42 | 0.8 | 45.8 | 0.69 | 66.1 |
| 34m | 4 | $\mu_{eff}$ + 2 OC | 39 | 0.77 | 48.1 | 0.71 | 65.2 |
| 34n | 4 | $\mu_{eff}$ + 2 OC | 42 | 0.77 | 47.9 | 0.68 | 66 |

The five-term equations 34a, 34b and 34c (constant term+2 attenuation coefficient terms+2 OC terms) show the evidence of overfitting. The equations 34d, 34e and 34f are a two-term equation (constant term+attenuation coefficient term) based on various wavelengths and the inclusion criteria. All have good calibration and prediction parameters, and distribution in the A and B zones of the Clarke Error Grid. The attenuation coefficient term at 592 nm (the highest absorbance for hemoglobin) has the best correlation parameters. A combination of

TABLE 5

Inclusion standard for using change in scattering and oxygen consumption

| Equation No. | Fitting equation | Inclusion standard |
|---|---|---|
| 34a | $[G] = a_0 + a_1*\{d[Ln(R_4/R_1)]/dt\}_{592\,nm} +$ | a, b, c |
| 34b | $a_2*\{d[Ln(R_4/R_1)]/dt\}_{880\,nm} +$ | a, b, $-0.8 < dLn(R_{880})/dt < 0.3$ |
| 34c | $a_3*[d(OC)/dt]@r_2 + a_5*[d(OC)/dt]r_3$ | a, b, $-1.0 < dLn(R_{880})/dt < +1.0$ |
| 34d | $[G] = a_0 + a_1*\{d[Ln(R_4/R_1)]/dt\}@592\,nm$ | B |
| 34e | $[G] = a_0 + a_1*\{d[Ln(R_4/R_1)]/dt\}_{880\,nm}$ | $-0.8, dLn(R_{880})/dt < +0.3$ |
| 34f | $[G] = a_0 + a_1*\{d[Ln(R_4/R_1)]/dt\}_{880\,nm}$ | $-1.0, dLn(R_{880})/dt < +1.0$ |
| 34g | $[G] = a_0 + a_1*\{d[Ln(R_4/R_1)]/dt\}_{592\,nm} +$ | b, $0.8 < dLn(R_{880})/dt < +0.3$ |
| 34h | $a_2*\{d[Ln(R_4/R_1)]/dt\}_{880\,nm}$ | b, $-1.0 < dLn(R_{880})/dt < +1.0$ |
| 34i | $[G] = a_0 + a_3*[d(OC)/dt]r_2$ | A |
| 34j | $[G] = a_0 + a_5*[d(OC)/dt]r_3$ | A |
| 34k | $[G] = a_0 + a_3*[d(OC)/dt]r_2 + a_5*[d(OC)/dt]\,r_3$ | A |
| 34l | $[G] = a_0 + a_1*\{d[Ln(R_4/R_1)]/dt\}_{592\,nm} +$ $a_3*[d(OC)/dt]@r_2 + a_4*[d(OC)/dt]@r_3$ | a, b |
| 34m | $[G] = a_0 + a_2*\{d[Ln(R_4/R_1)]/dt\}_{880\,nm} +$ $a_3*[d(OC)/dt]@r_2 + a_4*[d(OC)/dt]@r_3$ | a, $-0.8 < dLn(R_{880})/dt < +0.3$ |
| 34n | $[G] = a_0 + a_2*\{d[Ln(R_4/R_1)]/dt\}_{880\,nm} +$ $a_3*[d(OC)/dt]@r_2 + a_4*[d(OC)/dt]@r_3$ | a, $-1.0 < dLn(R_{880})/dt < +1.0$ |

A linear least square regression analysis was used for constructing pentanomial, tetranomial, trinomial, and binomial regression models in combinations of calculated oxygen consumption, calculated attenuation functions, and noninvasively measured glucose concentrations. The calibrated standard error and calibrated correlation coefficient were determined with respect to the respective first days of a study. The constructed models were used for predicting a glucose concentration from a data point at a later date. The data of the respective patients were separately processed. The calculated all two attenuation terms at 592 and 880 nm provides the three-term equations 34g and 34h, which results in improving the two-term equations 34d, 34e and 15f.

The use of OC term is shown in the equations 34i to 34k. The equations 34i and 34j are a two-term equation, and 34k is a three-term equation having two OC terms. The data shown in Table 6 shows the calibration and prediction capability of three OC models. By adding a $\mu_{eff}$ term to the equation 34k, the equations 34l, 34m and 34n are provided. All these three models result in giving a slight improvement of calibration to 34k. The time window in which this calculation is performed extended from 5 sec to 60 sec from the probe-skin interaction.

Selection of Optimal Time Interval

In this embodiment, the equation 34k was applied to an analysis of 6 patients. The equation 34k is a three-term model consisting of a constant term and two OC terms. The data on day 1 and day 2 were used in a calibration set. The data point on day 3 was used as a prediction set for each patient. A cumulative Clarke Error Grid was constructed for data points of all the patients, and overall calibration and prediction parameters were calculated. Ten time intervals were selected from 5 sec to 60 sec of the probe-skin interaction windows and as a result, time intervals between 55 sec and 30 sec were provided. The number of time points in the selected intervals is between 12 and 7. The calculation results are shown in Table 7.

The results in Table 7 show that the use of a time interval between 30 sec and 60 sec consequently provides a better calibration and prediction result. Because data was used in calculation, the use of a delay time of 30 sec from the initiation of the probe-skin contact reduced the contribution of skin-probe adaptation to correlation to the minimum, therefore, it had the best correlation with glucose.

TABLE 7

Effect of changing time window ranging from 5 sec to 60 sec using three terms (constant term and two oxygen consumption terms)

| Equation | Start/finish time (sec) | Δt (sec) | n | $r_c$ | SEC | $r_p$ | SEP |
|---|---|---|---|---|---|---|---|
| 34k-0 | 5/60 | 55 | 12 | 0.75 | 51.0 | 0.74 | 62.9 |
| 34k-1 | 10/60 | 50 | 11 | 0.76 | 49.3 | 0.72 | 62.8 |
| 34k-2 | 15/60 | 45 | 10 | 0.78 | 47.7 | 0.69 | 66.3 |
| 34k-3 | 20/60 | 40 | 9 | 0.78 | 47.2 | 0.7 | 63.4 |
| 34k-4 | 25/60 | 35 | 8 | 0.78 | 47.1 | 0.75 | 62.5 |
| 34k-5 | 30/60 | 30 | 7 | 0.80 | 45.6 | 0.83 | 59.0 |
| 34k-6 | 5/55 | 50 | 11 | 0.75 | 52.2 | 0.73 | 69 |
| 34k-7 | 10/55 | 45 | 10 | 0.76 | 48.8 | 0.72 | 61.6 |
| 34k-8 | 15/55 | 40 | 9 | 0.77 | 46.7 | 0.70 | 64.7 |
| 34k-9 | 20/55 | 35 | 8 | 0.8 | 44.9 | 0.7 | 67.5 |
| 34k-10 | 20/55 | 30 | 7 | 0.82 | 42.5 | 0.72 | 69.0 |

A similar result was obtained when the equation 34l which is a four-term model including a $\mu_{eff}$ term at 592 nm and two OC terms was used. The equation 34m is also a four-term model including a $\mu_{eff}$ term at 880 nm and two OC terms. It was shown by calculation that the use of a time interval between 30 sec and 60 sec consequently provides a better calibration and prediction model whether a three-term model is used or a four-term model is used. The use of a time interval of 30 sec reduces the contribution of skin-probe adaptation to correlation to the minimum.

The time intervals were from 30 to 60 sec, however, 7 data points are used in calculation of rates. The overall prediction correlation coefficient values are higher than those shown in Table 6, in which a complete time window ranging from 5 to 60 sec was used in calculation.

TABLE 8

Body-probe equilibration, Best models after setting equilibration time of 30 sec of body-probe

| Equation | $r_c$ | SEC | $r_p$ | SEP | % in A + B zone | % in C + D zone | % in E zone |
|---|---|---|---|---|---|---|---|
| 34k-5 | 0.80 | 45.6 | 0.83 | 59.0 | 94.7 | 5.3 | 0 |
| 34l-5 | 0.86 | 39.4 | 0.80 | 58.6 | 94.7 | 5.3 | 0 |
| 34m-5 | 0.76 | 48.8 | 0.72 | 61.6 | 94.4 | 5.6 | 0 |

In this embodiment, models consisting of various three terms of oxygen consumption only were attempted.

Generalized equation is as follows.

$$[G]=a_0+a_1*[F(OC)_n@r_i-F(OC)_n@r_j]\pm a_2*[F(OC)_m@r_i-F(OC)_m@r_j] \quad (35)$$

The functions of F(OC)1 and F(OC)2 were defined as follows before.

$$F(OC)_1=0.527*\{36.75*\text{Ln}[(R_{940})_t/(R_{940})_0]-\text{Ln}[(R_{592})_t/(R_{592})_0]\} \quad (27)$$

$$F(OC)_2=3.2022\{4.6566\text{Ln}[(R_{940})_t/(R_{940})_0]-\text{Ln}[(R_{660})_t/(R_{660})_0]\} \quad (33)$$

A three-term model in which a combination of F(OC)1 and F(OC)2 at different light source-detector distances is used provides the following equation.

$$[G]=a_0+a_1*[F(OC)_1@r_2-F(OC)_1@r_1]\pm a_2*[F(OC)_2@r_2-F(OC)_2@r_1] \quad (36)$$

Four oxygen consumption functions were calculated, however, the fitting equations have only three terms. When a combination of each of two OC functions at various light source-detector distances are used, the number of terms in the fitting equations is reduced from five to three, which reduces the possibility of constructing an overfitting line of data to the minimum. Various modifications of the equation 36 are as follows.

$$[G]=a_0+a_1F(OC)_1@r_1-a_2*F(OC)_1@r_2 \quad (37)$$

$$[G]=a_0+a_1F(OC)_2@r_1-a_2*F(OC)_2@r_2 \quad (38)$$

$$[G]=a_0+a_1*[F(OC)_1@r_2-F(OC)_1@r_1]+a_2*[F(OC)_2@r_2-F(OC)_2@r_1] \quad (39)$$

$$[G]=a_0+a_1*[F(OC)_1@r_2-F(OC)_1@r_1]+a_2*[F(OC)_2@r_2-F(OC)_2@r_1] \quad (40)$$

These equations were used for analyzing data for the patient 1001. The OC function is a logarithmic function, therefore, two subtractions as the case of a term of difference between two OC terms in (37) and (38) and $F(OC)_1$ and $F(OC)_2$ in the equation 40 represents a ratio term of a localized reflectance ratio at two light source-detector distances.

The data points of patients were collected in a period of 7 days. 16 out of 30 data points were passed the inclusion criteria. An average of 4×15 sec regions of time response as described above was used. In the calibration, 12 data points from day 1 to day 3 in the clinical study were used, and in the prediction, 4 data points from day 5 to day 7 in the clinical study were used. The results are shown in FIG. 7A to FIG. 7D.

The equation 37 is a three-term equation including a constant and a difference between two $F(OC)_1$ terms. The regression coefficient in the equation 37 is as follows.

$$[G]=195.2+432.3*F(OC)_1@r_1-391.6*F(OC)_1@r_2 \quad (37a)$$

Figure 7A:
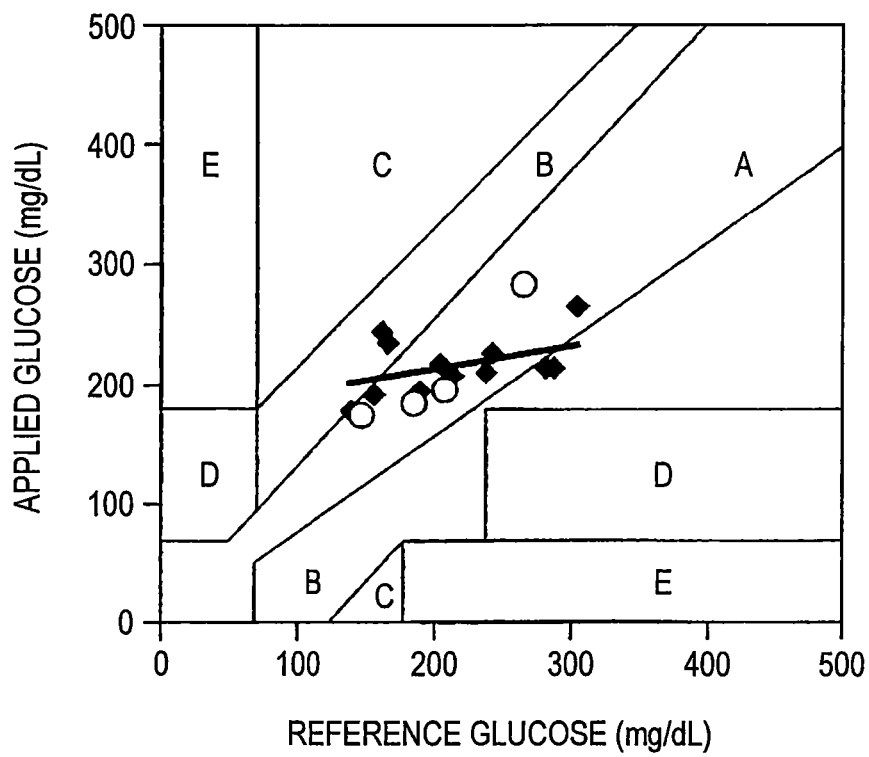
FIG. 7A is a Clarke Error Grid diagram for noninvasive measurement of glucose using the equation 37. Lozenges indicate calibrated data points and circles indicate predicted glucose values. The line is an approximation line between predicted and actual glucose values.

The data are plotted on FIG. 7A. The calibration and prediction parameters are good as shown in Table 9. The four predicted glucose values fall in the A zone of the Clarke Error Grid. As shown in Table 10, by linearly approximating the four predicted glucose values to the measured glucose values, an equation: $r^2=0.19$ is generated.

In still another embodiment, the equation 38 was used for analyzing the data of a subject No. 1001. The three-term approximate linear equation 38, the coefficients $a_0$, $a_1$ and $a_2$ obtained by calibration of two variables are provided in the equation 38a.

$$\text{Glucose}=167.9+7351.3*F(OC)_2@r_1-7985.2*F(OC)_2@r_2 \quad (38a)$$

Figure 7B:
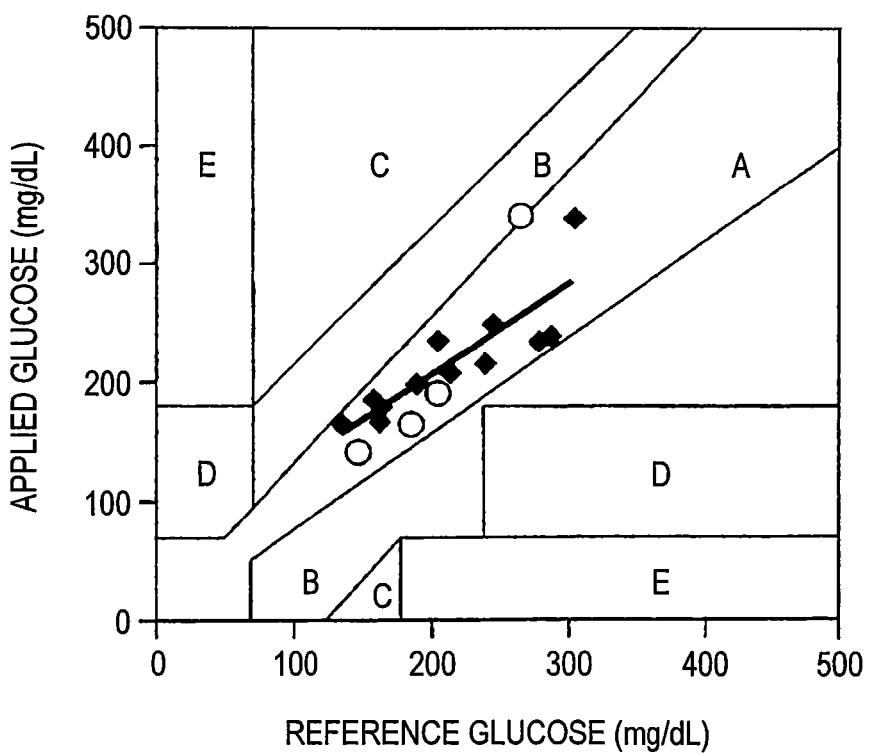
FIG. 7B is a Clarke Error Grid diagram for noninvasive measurement of glucose using the equation 38. Lozenges indicate calibrated data points and circles indicate predicted glucose values. The line is an approximation line between predicted and actual glucose values.

The data are plotted on FIG. 7B. The calibration and prediction parameters are good as shown in Table 9. The four predicted glucose values fall in the A zone of the Clarke Error Grid. As shown in Table 10, by linearly approximating the four predicted glucose values to the measured glucose values, a high correlation function: $r^2=0.75$ is generated. The use of $F(OC)_2$ consequently provides a better correlation with respect to this patient.

In still another embodiment, the equation 39 was used for analyzing the data of a subject No. 1001. The three-term approximate linear equation 39, the coefficients $a_0$, $a_1$ and $a_2$ obtained by calibration of two variables are provided in the equation 39a.

$$[G]=178.7+115.2*(F(OC)_1@r_2-F(OC)_1@r_1)-8303.9*(F(OC)_2@r_2-F(OC)_2@r_1) \quad (39a)$$

Figure 7C:
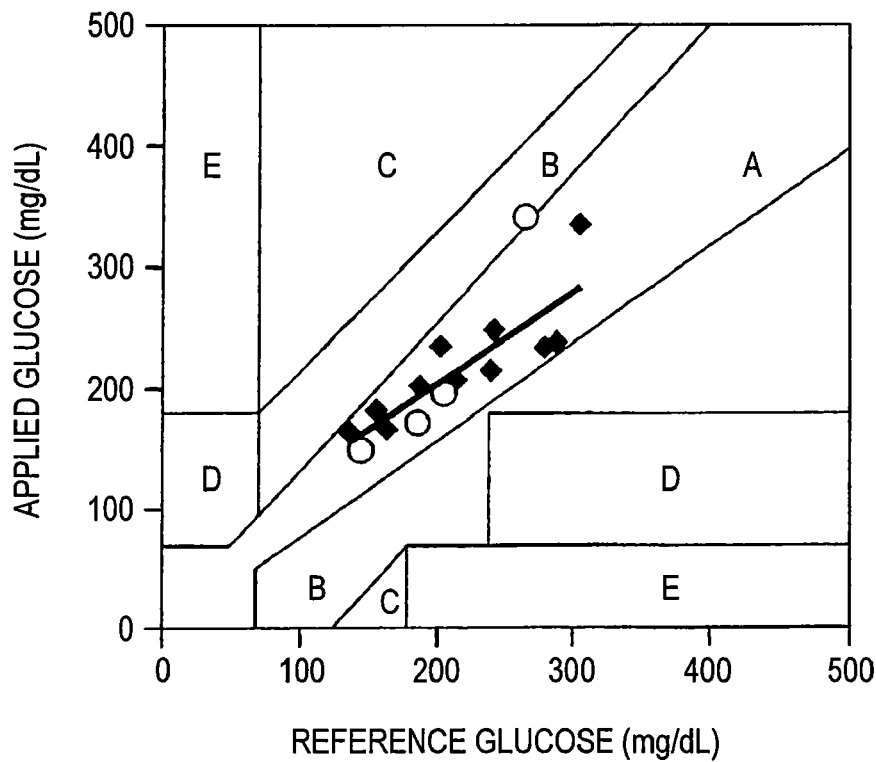
FIG. 7C is a Clarke Error Grid diagram for noninvasive measurement of glucose using the equation 39. Lozenges indicate calibrated data points and circles indicate predicted glucose values. The line is an approximation line between predicted and actual glucose values.

The data are plotted on FIG. 7C. The calibration and prediction parameters are good as shown in Table 9. The four predicted glucose values fall in the A zone of the Clarke Error Grid. As shown in Table 10, by linearly approximating the four predicted glucose values to the measured glucose values, a high correlation function: $r^2=0.75$ is generated.

Figure 7D:
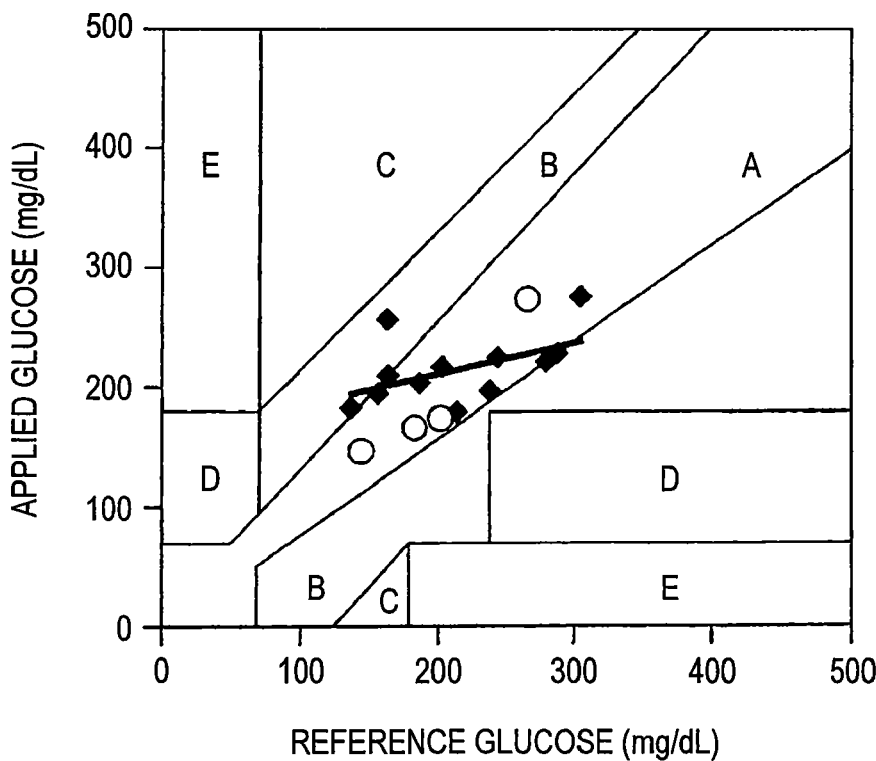
FIG. 7D is a Clarke Error Grid diagram for noninvasive measurement of glucose using the equation 40. Lozenges indicate calibrated data points and circles indicate predicted glucose values. The line is an approximation line between predicted and actual glucose values.
Figure 8:
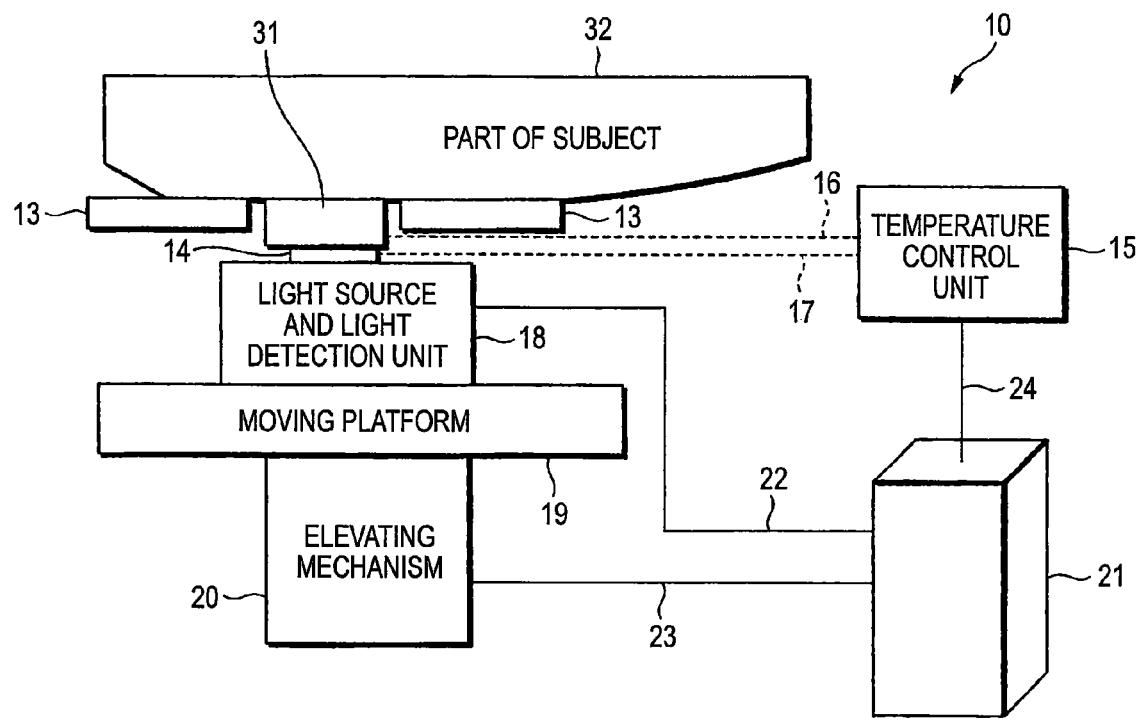
FIG. 8 is a diagram showing a configuration of an apparatus for noninvasive measurement according to a second embodiment.

FIG. 7D shows the use of the equation 40 for analyzing the data of a subject No. 1001. The equation 40 is a three-term approximate linear equation including a constant, a difference between two $F(OC)_1$ terms and a sum of two $F(OC)_1$ terms. The first parenthesis is a difference between two $F(OC)_1$ values which consequently provide localized reflectance ratios at two light source-detector distances $r_1$ and $r_2$. The second term in the parenthesis is a sum of two $F(OC)_2$ values which consequently provide a multiplication. The three-parameter approximate linear equation, the coefficients $a_0$, $a_1$ and $a_2$ obtained by calibration of two variables are provided in the equation 40a.

$$[G]=154-529.8*(F(OC)_1@r_2-F(OC)_1@r_1)-1351*(F(OC)_2@r_2-F(OC)_2@r_1) \quad (40a)$$

TABLE 9

Linear least squares calibration and prediction parameters in three-term oxygen consumption model

| Equation/FIG. | Calibration Number of data points = 12 Average [G] = 217.7 mg/dl | | | Prediction Number of data points = 4 Average [G] = 203.8 mg/dl | | |
|---|---|---|---|---|---|---|
| | $r_c$ | SEC | SEC % | $r_p$ | SEP | SEP % |
| 37/FIG. 7A | 0.44 | 48.1 | 22.1 | 0.94 | 15.9 | 7.8 |
| 38/FIG. 7B | 0.86 | 27 | 12.4 | 0.95 | 40.2 | 19.7 |
| 39/FIG. 7C | 0.87 | 26.7 | 12.3 | 0.95 | 38 | 18.6 |
| 40/FIG. 7D | 0.51 | 46 | 21.1 | 0.96 | 19.3 | 9.5 |

As shown in Table 9, the equations 38 and 39 provide the best calibration parameters and good prediction parameters.

TABLE 10

Linear relationship between noninvasively predicted glucose values (Y) and reference glucose values (X)

| Regression model | Y = ax + b | Correlation coefficient $r^2$ |
|---|---|---|
| Equation 37/FIG. 7A | Y = 0.1909x + 176.06 | 0.1909 |
| Equation 38/FIG. 7B | Y = 0.7455x + 55.367 | 0.7455 |
| Equation 39/FIG. 7C | Y = 0.7502x + 54.323 | 0.7502 |
| Equation 40/FIG. 7D | Y = 0.2593x + 161.26 | 0.2593 |

The use of three terms (a constant term+two oxygen consumption terms) derived calibration and prediction models of a change in glucose concentration in a diabetic patient over a period of 7 days. Oxygen consumption is calculated at two light source-detector distances in the localized reflectance measurement. This embodiment is directed to calibration of one patient. The coefficients in the model or the types of OC functions depend on a disease condition, a type of drug used by a patient, and a diabetic period, and vary depending on a patient.

Second Embodiment

Hereinafter, explanation will be made with reference to a second embodiment.

First, an outline of this embodiment will be described. Ahead of noninvasive measurement by a measurement probe, by adapting (conforming) the shape of the measurement probe to a skin part of a subject, the effect of skin-probe interaction on signals measured is reduced. When a structural substance such as a measurement probe comes into contact with the skin, several mechanical and thermal effects are caused. First, the skin is stretched for adapting the shape of the probe. The contact between the skin and the measurement probe changes over time as the skin is adapted to the shape of the probe. The adaptation of the rigid metal probe to the soft skin can appear as a time dependent change in light signal to be measured. Secondly, the probe subsequently presses the tissue to cause local occlusion and further affects blood flow. As a third effect, pressing of the probe against the skin causes a change in packing of scattering center per unit area and compression of the skin. However, this tissue packing effect is expected to be small by the pressure discussed in this embodiment. As a fourth effect, a heat is transferred from the probe to the skin or vice versa depending on the thermal conductivity of a material of the probe and a difference in the temperature between the tissue and the probe. The heat transfer between the skin and the probe induces a temporary temperature change at a measurement site. All these mechanical and thermal effects induce a change in signals to be measured independently of the concentration of an analyte to be measured.

In order to ensure a close contact, effective optical and thermal binding and reduce such a change in a signal independent of a time dependent analyte to the minimum, it is necessary to adapt the skin for conforming to the measurement probe ahead of the step of detecting an analyte.

The method of adapting the skin includes use of a small amount of silicone oil to be applied to the skin of a subject for enhancing the thermal conductivity. An excess amount of oil can make the probe slip on the skin, and an insufficient amount of oil causes incomplete thermal binding. For the purpose of eliminating a gap between the probe and the skin, in addition to the oil, other binding jell can be used. However, this reduces a surface reflection loss. Further, in order to realize a desired temperature in a tissue layer of a subject, such a liquid or jell enhances the thermal binding and facilitates the heat transfer between the skin and the probe.

In the method of this embodiment, a temperature-modulated localized reflectance probe can be used. The temperature-modulated probe has a light introduction fiber and several light collection fibers. The light collection fibers are disposed at a short distance from the light introduction fiber. The use of this type of probe was discussed in the academic papers of Kalil et al., "Temperature modulation of the visible and near infrared absorption and scattering coefficients of intact human skin", J. Biomedical Optics, 2003; 8: 191-205, Yeh et al., "Near infrared Thermo-Optical Response of The Localized Reflectance of Intact Diabetic and Non-Diabetic Human Skin", J. Biomedical Optics, 2003; 8: 534-544, Yeh et al., "Tracking Blood Glucose Changes in Cutaneous Tissue by Temperature-Modulated Localized Reflectance Measurements" Clinical Chemistry, 2003; 49: 924-934, and Khalil et al., "Response of near IR localized reflectance signals of intact diabetic human skin to thermal stimuli" SPIE Proceedings 2003; 5086: 142-148. These publications describe the use of silicone oil for enhancing thermal binding as described in U.S. Pat. No. 6,654,620. These academic papers did not disclose a method for enhancing the mechanical adaptation of the skin to a measurement probe.

U.S. Pat. Nos. 5,795,305, 5,924,996, US Patent Application Publication No. 2005/0,124,868 and European Patent Application Publication No. 1537822 did not take the skin-probe adaptation effect on the optical and thermal signals into consideration. U.S. Pat. No. 5,978,691 did not disclose or take into consideration a time window for reducing the tissue-probe adaptation effect on the measurement to the minimum. In U.S. Pat. No. 5,978,691, a temperature-induced change in the hemoglobin equilibrium is measured. U.S. Pat. No. 5,978,691 does not disclose a method for enhancing the mechanical adaptation of the skin to a measurement probe.

In this embodiment, noninvasive measurement is divided into two major steps. That is, a skin adaptation step and a measurement step. The skin adaptation step is performed ahead of the measurement step. In the skin adaptation step, the measurement probe with a high rigidity is brought into contact with a skin part which is an objective site of a subject and the skin part is adapted to the shape of a surface thereof (the shape of an interface region).

By bringing an adaptation device (also referred to as a stretching device) which has a shape similar to the measurement probe into contact with a skin part ahead of the contact between the measurement probe and the skin, the skin part is stretched. This contact is carried out under a pressure that is higher than a pressure applied by the measurement probe during the measurement. The contact between the adaptation device and the skin is maintained for a certain period of time. The adaptation device may be provided as a separate body from the measurement probe, or may be shared with the measurement probe.

For example, an example of a case in which the adaptation device and the measurement probe are shared will be described. In the skin adaptation step and the measurement step, the measurement probe which also serves as the adaptation device moves up and down and comes into contact with a skin part of an objective site of a subject. A part of the subject is irradiated with an optical signal from a light source and light detection unit through an optical fiber unit, and also a reflected wave from the part of the subject is detected at the light source and light detection unit through the optical fiber unit. In the skin adaptation step, the measurement probe which also serves as the adaptation device comes into contact with the part of the subject, but may not detect the light signal. On the other hand, in the measurement step, the measurement probe which also serves as the adaptation device detects the light signal at a desired time in which the measurement probe is contacted with the part of the subject.

An example of a case in which the adaptation device constituting the measurement probe and the optical fiber unit are separated will be described. In the skin adaptation step, the adaptation device moves up and down, but the optical fiber unit does not move. In the measurement step, the adaptation device and the optical fiber unit move up and down in conjunction with each other. A case in which the adaptation device is provided as a separate body and functions also as a part of the measurement probe may be applied. In the adaptation device, an optical window is provided, and in the skin adaptation step, the adaptation device moves up and down, and in the measurement step, the optical fibers, the light source and light detection unit move up and down as the measurement probe in conjunction with the adaptation device.

Subsequently, the contact with the adaptation device is relieved. The measurement probe is brought into contact with the skin which has been consequently adapted, i.e., stretched such that it is conformed to the shape of the surface of the probe for performing measurement.

In this embodiment, a method for adapting the skin of a subject in order to adapt the skin to the shape of a detecting device which is brought into contact with the skin for noninvasive determination of glucose in a tissue of the subject includes the steps of:

a) bringing a device which has a shape similar to a measurement probe into contact with a skin part of a subject thereby to stretch the skin part of the subject and allowing this contact to achieve an effect under a pressure that is higher than a pressure applied by the measurement probe to the skin during noninvasive measurement;

b) maintaining this contact for a predetermined period of time;

c) relieving the contact between the skin and the skin adaptation device;

d) bringing a temperature-modulated localized reflectance measurement probe into contact with a tissue of the body under a pressure per unit area that is lower than a pressure applied by the adaptation probe;

e) performing noninvasive measurement for collecting signals emitted from the tissue;

f) deriving a calibration relationship between a combination of physically and physiologically associated parameters and a glucose concentration in the body; and g) using the established calibration relationship for predicting a glucose concentration in the human body.

The measurement probe is controlled by a spring. At the start of the respective measurements, a subject sits on a chair, places the left arm on a body interface receiving stand and adjusts the distance between an arm tray and a grip so as to give a comfortable position. Then, the subject pushes in a double-probe head supported by a spring by the right hand and starts countdown. When the count becomes zero, an operator clicks the start icon, and then, the subject relieves the double-head probe for bringing it into contact with the skin. The movement of the probe is not controlled, and a force applied by the spring determines the displacement of the skin. The contact between the probe and the skin at a fixed temperature for about 120 sec can reduce the effect of adapting the skin to the measurement probe on a signal to the minimum.

Figure 10:
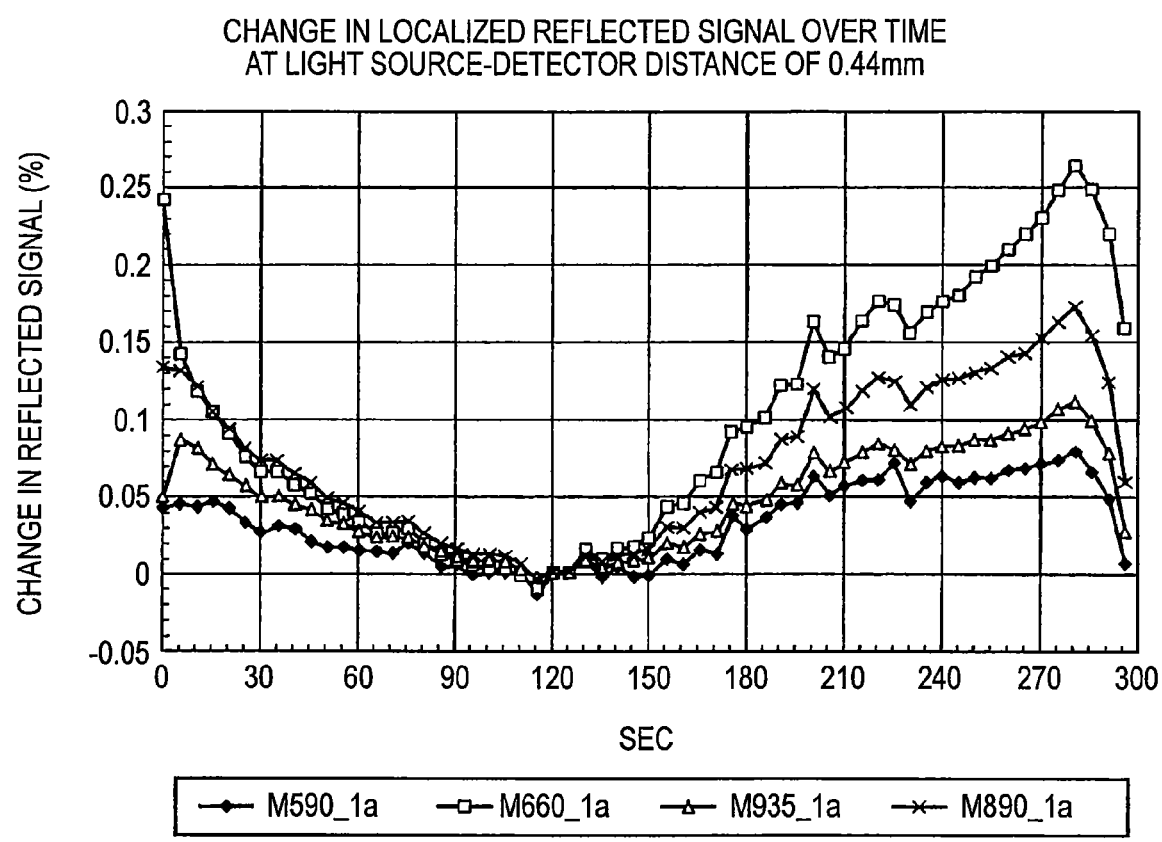
FIG. 10 is a graph showing a time course of a reflected signal by a contact time of a measurement probe with the skin in this embodiment.

FIG. 10 shows a time course of a change in signal in this experiment at four different wavelengths: 590 nm, 660 nm, 890 nm and 935 nm. FIG. 10 describes a percentage change in localized reflected signal as measured by a probe similar to one described in U.S. Pat. No. 6,662,030 at a distance of 0.44 mm from a radiation fiber. The data relates to the skin of a forearm of a volunteer (subject 1015, implementation D, Sep. 13, 2003). The data is represented as a percentage change in signal normalized to the data point of 120 sec. The first data point at 0 sec is the point at 3 sec from the contact, and it was a time required for collecting data and transmitting it from a data board to a computer. The subsequent data point starts from the first data point recorded. Because the probe reduced heat transfer between the skin and the measurement probe to the minimum, the temperature was maintained at 30° C. very close to the normal temperature of the skin which is generally from 28° C. to 32° C. It is apparent that the percentage change in signal greatly fluctuates in the initial 30 sec. The majority of the percentage change in signal occurred in the initial 10 sec. The temperature of the probe was maintained at 30° C. very close to the normal temperature of the skin which is generally from 28° C. to 32° C., therefore, the majority of this change was caused by the mechanical adaptation of the skin to the measurement probe. The pressure applied to the skin by the probe was 45 g/cm$^2$. In order to facilitate thermal and optical binding, silicone oil was applied to the skin. The change in signal decreases as the time proceeds and reaches a complete equilibrium state between 90 sec and 120 sec. The temperature changed from 120 sec. The change in signal in the initial 120 sec in which the temperature of the probe was maintained at 30° C. reached 0 to 0.25%. By changing the temperature only by 12° C. over 180 sec, a large change in localized reflectance by the skin-probe interaction at a fixed temperature close to the normal skin temperature was induced, and this is caused by the mechanical adaptation of the skin to the probe.

The change in signal by the mechanical adaptation of the skin decreases as the time proceeds and reaches a complete equilibrium state between 90 sec and 120 sec. This time is too long for waiting for practical noninvasive determination of glucose, and during this long contact, a possibility that the probe moves against the skin may be accompanied. It is important to reduce the effect of adaptation of the skin to the probe on the signals measured by previously adapting the skin ahead of the measurement. In order to achieve the effect of the adaptation of the skin to the measurement probe in a shorter probe contact time, other methods have to be discovered. FIG. 10 shows a time course of a localized reflected signal in the skin of a volunteer. The temperature of the measurement probe was maintained constant at 30° C. for 120 sec, and then raised at a rate of 4° C. per minute.

Still another aspect of this embodiment is a method for performing noninvasive measurement in a tissue of a subject in order to determine an analyte concentration in the tissue of the subject, and the method includes adapting the skin of a subject for adapting its shape to the shape of a detection device to be brought into contact with the skin for noninvasive quantification of glucose in a tissue liquid of the subject, and includes the steps of:

a) providing an apparatus for noninvasive measurement of glucose having at least one temperature-modulated measurement probe which can receive displacement to be controlled for applying a control pressure to the tissue to be optically measured and is attached to a moving mechanism;

b) bringing the measurement probe into contact with a skin part of a subject thereby to stretch the skin part, moving a platform with respect to a defined displacement to adapt the skin part for conforming its shape to the shape of the probe during the subsequent optical measurement, and allowing a first contact between the skin and the measurement probe under these conditions to achieve an effect for a limited period of time;

c) moving the platform for relieving the contact between the skin and the measurement apparatus and the tissue;

d) bringing a tissue of the body into contact with the measurement apparatus described in (a) having at least one temperature-modulated measurement probe at a displacement which is smaller than the displacement given in the step (c) and under a pressure applied by an adaptation probe;

e) measuring a change in signals over a specific period of time from the skin-probe contact;

f) deriving a calibration relationship between a combination of physically and physiologically associated parameters and a glucose concentration in the body; and g) using the established calibration relationship for predicting a glucose concentration in the human body.

The method of this embodiment reduces the effect of the skin-probe interaction on the measured signals by effecting the adaptation of the skin to the measurement probe ahead of the noninvasive measurement. U.S. Pat. Nos. 5,785,305, 5,924,996 and 5,978,691 did not disclose a method for adapting the skin to a measurement probe for reducing the skin-probe adaptation effect on the measurement to the minimum.

The method of this embodiment is independent of the measurement method or the probe to be used. The measurement probe may be a light-absorbing probe using NIR wavelength as described by Maruo (U.S. Pat. No. 5,975,841), or a light-scattering probe as described by Gratton (U.S. Pat. No. 5,492,118) and Simonsen (U.S. Pat. No. 5,551,422), or Khalil et al. (U.S. Pat. No. 6,662,030).

The adaptation of the skin by stretching the skin by a device which has a shape similar to the measurement probe can be involved in applying a pressure to the skin for 1 to 10 sec. Preferably, the pressure application time for inducing the adaptation of the skin to the shape of the probe is from 5 sec to 10 sec.

The pressure applied for conforming the skin to the probe is 2 to 5 times the pressure value applied to the skin by the measurement probe. The pressure is defined by a unit of g/cm$^2$ or a pound per square inch. Preferably, in order to reduce an uncomfortable feel by the pressure to the minimum, the pressure is 2 to 3 times the maximum value of the pressure applied to the skin by the measurement probe. The pressure value depends on the thickness of the skin, the degree of skin aging and a diabetic period and can vary depending on an individual. A high pressure can lead to occlusion of a blood vessel in the skin, and a low pressure can lead to an incomplete contact.

The pressure which we used before for measurement was generally in the range from 45 to 100 g/cm$^2$. A pressure lower than 30 g/cm$^2$ leads to an incomplete contact, and a pressure higher than 130 g/cm$^2$ applied for several tens of seconds leads to partial occlusion. Therefore, a stretching pressure ranging from 200 to 500 g/cm$^2$, preferably from 200 to 300 g/cm$^2$ stretches the skin thereby to adapt the skin to the measurement probe, and further, because a close contact with an optical element is achieved, the use thereof can be allowed in a limited time such as 10 sec.

By using a combination of time and pressure, it is possible to optimize the skin adaptation step so as to realize a necessary skin adaptation, and also to reduce pain by applying a pressure and an uncomfortable feel by the pressure application time to the minimum. Such a combination can include a high pressure in a short time or the lower limit of the pressure range in a long time. The magnitude of the displacement can depend on the properties of the skin, and can vary depending on an individual.

In the method for noninvasive measurement of the prior art, a binding liquid such as silicone oil, paraffin oil, perfluorohydrocarbon or a water-glycerol mixture was used for enhancing the thermal conductivity and reducing the reflection loss in the measurement of diffusion reflectance to the minimum. A jell or a cream such as a mixture of paraffin wax, an oil, water and an emulsifying agent can also be used in the method of this embodiment. Such an oil is preferably applied before applying a pressure. In order to prevent the adaptation device from slipping on the skin or incompletely contacting with the skin, it is preferred that such a binding liquid or jell is used in a small amount and the skin is uniformly covered therewith. A preferred method for applying the binding agent is described in U.S. patent application Publication Ser. No. 10/823,073, "Apparatus and method for applying binding agent to noninvasive optical sensor" filed on Apr. 13, 2004.

In the prior art, a method in which a permeable substance or a clearing solution is used for increasing the movement of water to the stratum corneum, reducing the scattering thereof and yielding transparent visible light is described. For example, an academic paper, Vargas G, Chan E K, Barton J K, Rylander H G, 3rd. Welch A J. Use of an agent to reduce scattering in skin, Lasers Surg Med., 1999; 24(2): 133-41 can be referred to. In this case, it is possible to take an image of lower blood vessels and perform optical measurement without interference from the stratum corneum. Some of these active substances are glycerol or a water-glycol mixture and a water-glycol-oleic acid mixture. It is possible to use the clearing solution in the method of this embodiment. The use of the clearing solution takes several minutes to affect the stratum corneum, therefore, it may be used first and wiped off, and then, a pressure may be applied. The water-glycol-oleic acid mixture can make the stratum corneum smooth, remove several surface flacks, whereby a better probe-skin contact can be achieved.

After the skin adaptation step, the measurement probe is brought into contact with the skin again, and a data stream generated by the measurement is collected over a given period of time. In a preferred mode of this embodiment, a data point in a range of time window is selected to be used in the calculation of the concentration of an analyte. In order to further reduce the tissue-probe adaptation effect on a signal to the minimum, this time window starts at several seconds from the initiation of the probe-skin contact.

The skin adaptation method of this embodiment can be used in several optical and non-optical methods. The absorbance and scattering methods, the thermal conductivity method and the method for infrared emission from the skin can be used in the method of this embodiment. In particular, when there is a direct contact between a solid measurement probe and a malleable tissue such as skin, the method of this embodiment can be used in optical and non-optical measurements. Therefore, in a photoacoustic measurement in which light excites an absorber and an ultrasound measurement probe is brought into contact with the skin, a signal is affected by a sound speed in the tissue affected by compression of the skin, therefore, the improvement of tissue adaptation to the prove ahead of the measurement reduces an error due to compression of tissue.

In order to reduce the effect of the temperature of the skin on the optical properties of the skin, the temperature and the adaptation device are maintained at around the normal temperature of the skin, i.e., 28° C. to 32° C.

Hereinafter, a configuration of the apparatus for noninvasive measurement of this embodiment will be specifically described together with the method.

Figure 13A:
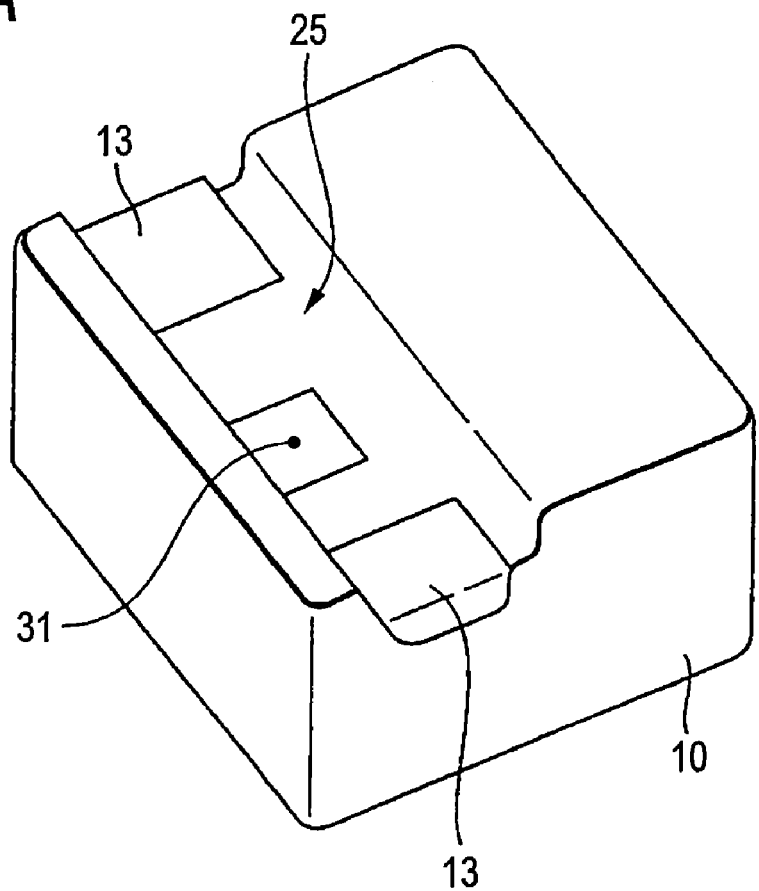
FIG. 13A is an external view of an apparatus for noninvasive measurement in this embodiment.
Figure 13B:
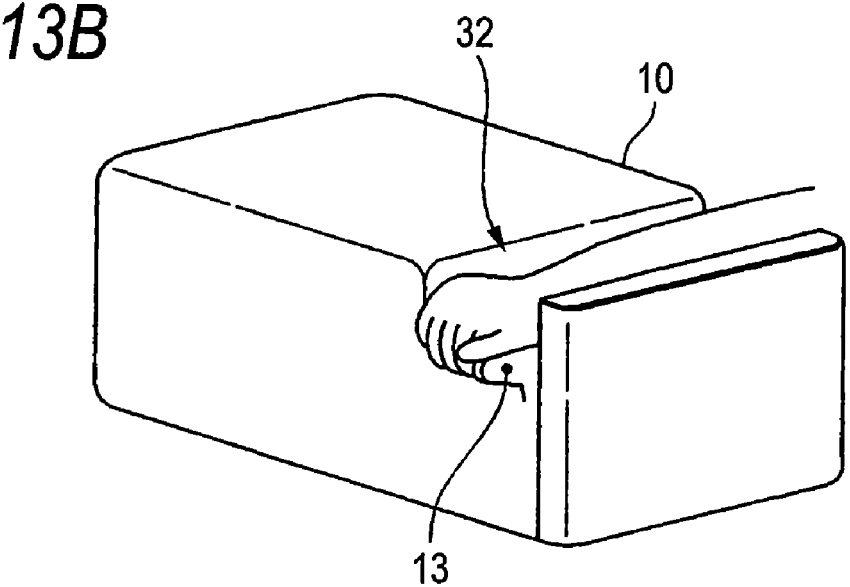
FIG. 13B is a view showing an appearance during measurement in this embodiment.

As a typical external view of an apparatus for noninvasive measurement according to this embodiment, as shown in FIG. 13A and FIG. 13B, an arm tray 25 which is caved in a groove shape is formed in a part of a housing of the apparatus 10. In a substantially center portion of the arm tray 25, the surface of a measurement probe 11 is exposed. At each of the both ends of the arm tray 25, a fixed platform 13 is provided. Upon measurement, a subject places an arm on the arm tray 25 such that a part (a measurement site) of the arm of the subject is contacted with the surface of the probe 10.

FIG. 1 shows a single-probe type apparatus for noninvasive measurement 10 according to this embodiment. The apparatus has the measurement probe 11 which is installed on the fixed platform 13 and comes into contact with a part of a subject, typically a part of an arm 12 and the skin thereof. The measurement probe 11, a temperature modulation element 14, a light source and light detection unit 18 are installed on a moving platform 19. A temperature control unit 15 has a feedback input 16 and a control output 17 with respect to the temperature modulation element 14. The vertical movement of the moving platform 19 for approaching and retreating from the part of a subject 12 is effected by an elevating mechanism 20 having a stepper motor, an elevating actuator and a spring. A computer 21 plays a role in total control for measurement and total control for an adaptation operation of a skin shape ahead of the measurement as well as data analysis by controlling the temperature control unit 15, the light source and light detection unit 18, and the movement of the moving platform 19 via control/signal lines 22, 23 and 24. The measurement method may be any of absorbance, reflectance, localized reflectance, photoacoustic spectroscopy and Raman spectroscopy.

A patient places an arm or other body part 12 on the fixed plat form 13 (see FIG. 13B). When noninvasive measurement is started, the computer 21 moves the moving platform 19 up toward the skin to press the measurement probe 11 against the skin by a step number n via the elevating mechanism 20 for an adaptation operation, which is characteristic in this embodiment, whereby the skin adaptation step is started. This state is maintained for a period of about 5 to 10 sec, and then relieved.

This process induces adaptation of the skin to the shape of the measurement probe 11, and in the subsequent noninvasive measurement step, a close contact between the measurement probe 11 and the skin is achieved. Thereafter, the computer 21 separates the moving platform 19 from the skin, and then, the data collection step is started by moving the measurement probe 11 and therefore the moving platform 19 toward the skin again by a step number (n-x) for causing a smaller displacement of the skin. x represents an arbitrary step number and this means that the elevating distance of the moving platform 19 in the measurement process is shorter than the elevating distance of the moving platform 19 in the adaptation process by a distance obtained by multiplying the reduced step number x by a step unit distance, in other words, the pressing force of the measurement probe 11 against the skin in the measurement process is reduced according to a distance obtained by multiplying the reduced step number x by a step unit distance from the pressing force of the measurement probe 11 against the skin in the adaptation process.

The computer 21 causes an operation of data collection from the light source and detection optical element 18 for a specific period of time, and processes the data. The use of the temperature modulation element 14, the temperature control unit 15, the feedback input 16 and the feedback control output 17 can reduce the signal drift due to uncontrolled heat transfer between the body and the probe to the minimum, and enables the examination of the effect of an induced temperature change on the signal.

Figure 9:
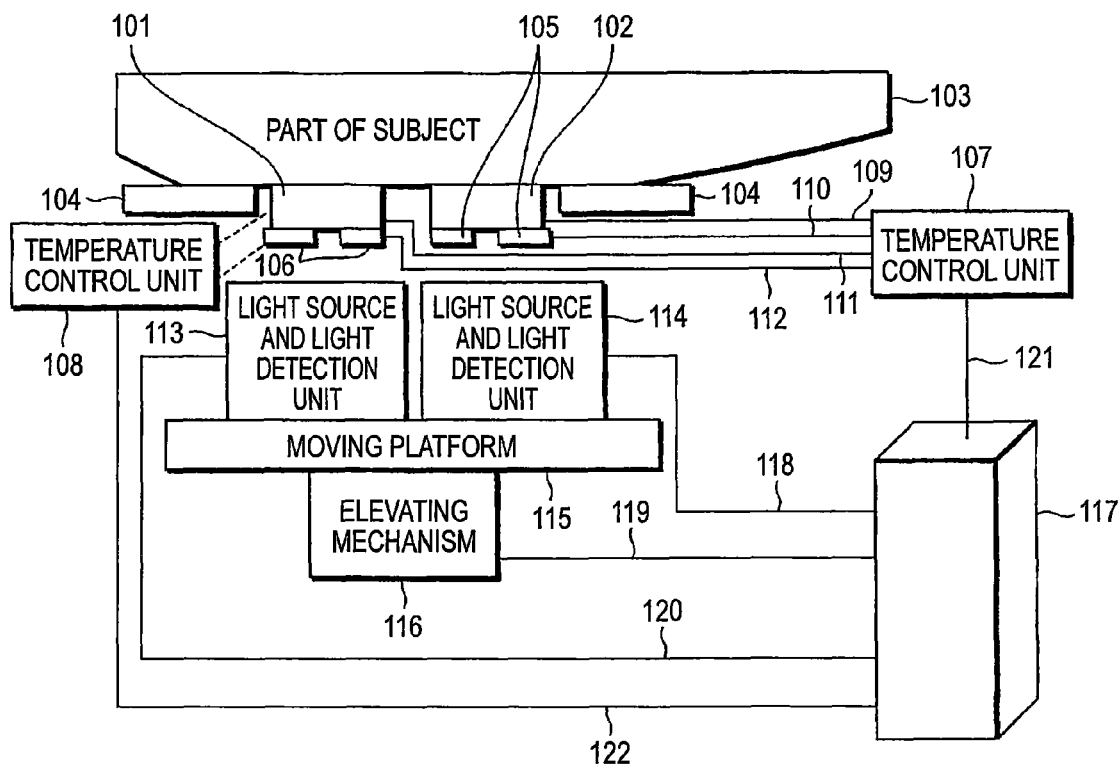
FIG. 9 is a diagram showing another configuration of an apparatus for noninvasive measurement according to this embodiment.

FIG. 9 shows a double-probe type apparatus for noninvasive measurement according to this embodiment. The apparatus has two measurement probes 101 and 102, which are installed on a fixed platform 104 and come into contact with a part of a subject 103. Temperature control units 107 and 108 having temperature modulation elements 105 and 106, feed back inputs 109 to 112 to a temperature modulator are provided for modulating the temperature of the respective measurement probes 101 and 102. The measurement probes 101 and 102 have light source and light detection units 113 and 114, respectively. The two measurement probes 101 and 102 are installed on a common moving platform 115. The vertical movement of the moving platform 115 is effected by an elevating device 116 having a stepper motor or an elevating actuator and a spring. A computer 117, which also performs data analysis, plays a role in total control for measurement and total control for an adaptation operation of a skin shape ahead of the measurement as well as data analysis by controlling the temperature control units 107 and 108 of the respective measurement probes 101 and 102, the light source and light detection units 113 and 114 and the movement of the moving platform 115 via control/signal lines 118 to 121.

A patient places an arm or other body part 103 on the fixed platform 104. Before noninvasive measurement is started, the computer 117 moves the moving platform 115 up toward the skin to press the measurement probes 101 and 102 against the skin by a step number n via the mechanism 116 for an adaptation operation. This state in which the measurement probes 101 and 102 are pressed against the skin is maintained for about 5 to 10 sec. This process induces adaptation of the skin to the shape of the measurement probes 101 and 102, and in the subsequent noninvasive measurement step, a close contact between the measurement probes 101 and 102 and the skin is achieved.

Subsequently, the computer 117 lowers the moving platform 115 for separating the measurement probes 101 and 102 from the skin.

The data collection cycle is started by moving the measurement probes 101 and 102 and therefore the moving platform 115 toward the skin again by a step number (n-x) for causing a smaller displacement of the skin.

The computer 117 causes an operation of data collection from the light source and detection optical elements 113 and 114 for a specific period of time, and processes the data. The use of the temperature modulation elements 105 and 106, the temperature control units 107 and 108, the feedback inputs and the control outputs 109 to 112 can reduce the signal drift due to uncontrolled heat transfer between the part of a subject 103 and the measurement probes 101 and 102 to the minimum, and enables the examination of the effect of an induced temperature change on the signal. The temperature of the respective measurement probes 101 and 102 is modulated separately, and various temperature changing steps can be used for the respective measurement probes 101 and 102.

In this connection, U.S. Pat. No. 6,662,030 describes a temperature-modulated localized reflectance probe which can be used in the method of this embodiment. The probe has a light introduction fiber and several light collection fibers disposed at a short distance from the light introduction fiber. The maximum distance between the center of the light collection fiber and the light collection fiber is less than 2 mm.

In this embodiment, a temperature-modulated localized reflectance measurement probe which is similar to a probe described in U.S. Pat. No. 6,662,030 by Khalil et al. and Khalil et al., J. Biomed. Opt. 2003; 8: 191-205, Yeh et al., J. Biomed. Opt. 2003; 8: 534-544, and Yeh et al., Clin. Chem. 2003; 49: 924-934 is used. The measurement of localized reflected signals using a temperature-modulated probe described in U.S. Pat. No. 6,662,030 (Khalil et al.) provides a light signal according to a temperature or a contact time between a probe at a given temperature and a part of the body.

Figure 11:
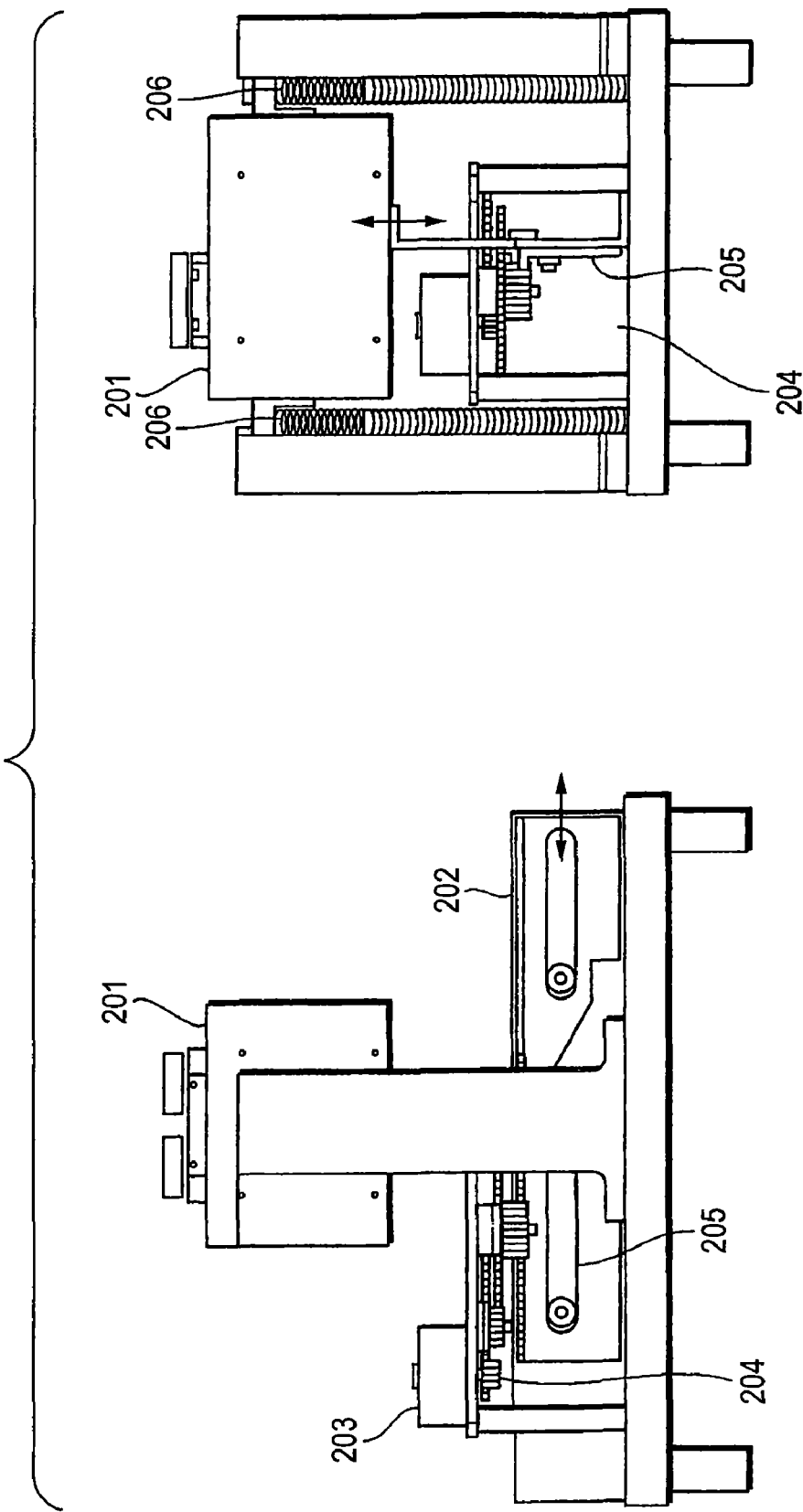
FIG. 11 is a structural diagram corresponding to FIG. 2.

FIG. 11 shows a structural example of an elevating device of this embodiment. An elevating actuator 202 includes a motor 203, a plurality of gears 204, a lever 205 and a spring 206. A probe 201 is moved in a vertical direction by moving the lever 206 installed on the bottom with the motor 203 and the gears 204. The moving distance of the upper and lower lateral face is generally 10 to 15 mm. The probe 201 is supported by the two springs 206. The springs 206 keep the contact pressure to the skin. The pressing power against the skin can be generally set to about 100 gf/cm$^2$.

Figure 12:
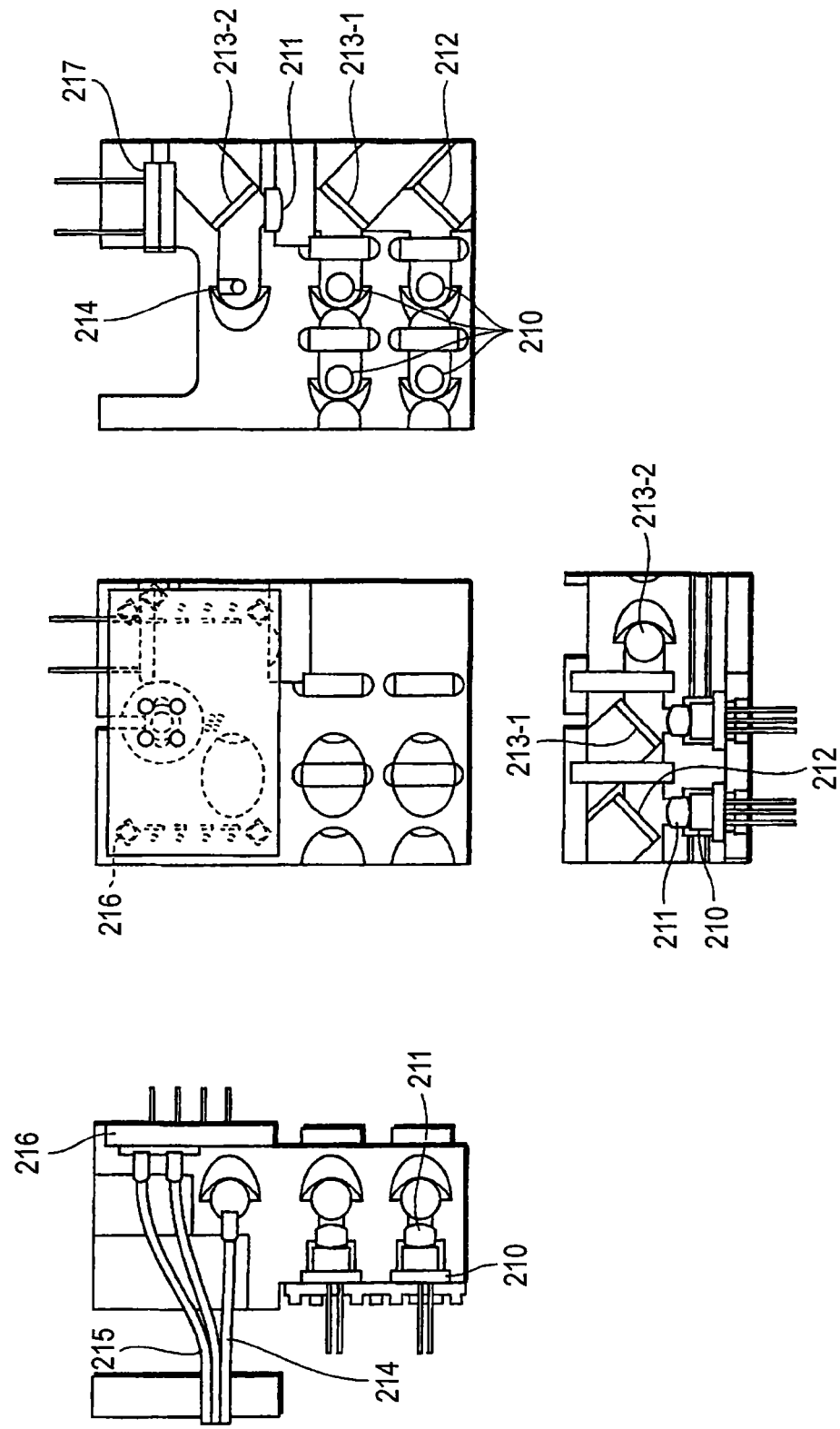
FIG. 12 is a diagram showing a structure of a light source and light detection unit of FIG. 8 and FIG. 9.

FIG. 12 shows a structure of a light source and light detection unit together with two measurement probes 201. The light source and light detection unit includes a light source 210, a lens 211, a mirror 212, half mirrors 213-1 and 213-2, an optical fiber for radiation 214, an optical fiber for signal detection 215, a photodiode (PD) for signal detection 216 and a photodiode (PD) for reference 217. The light source 210 emits one or more light beams. The light beams are collimated and combined by passing through the lens 211, the mirror 212 and the half mirror 213-1. The combined light beams pass through the optical fiber for radiation 214, and then illuminate the body. A part of the combined light beams is divided by the half mirror 213-2, and detected as a reference signal by the photodiode (PD) for reference 217. A part of the reflected signal from the body passes through the optical fiber for signal detection 215 at one or more positions disposed at an appropriate distance from the radiation spot, and then, the reflected signal is detected by a light detector (PD) for signals 216 as a reflected signal.

In this connection, the present invention is not limited to the above embodiments as such, and may be embodied in implementation phase by modifying the components without departing from the scope of the invention. Further, various inventions can be created by appropriately combining the plurality of components disclosed in the above embodiments. For example, several components may be eliminated from all the components disclosed in any of the embodiments. Further, the components of different embodiments may be appropriately combined.

According to an aspect of the present invention, in a method for noninvasive measurement of glucose and an apparatus for noninvasive measurement of glucose, a temperature change is induced in the human skin, localized reflectance signals at several defined light source-detector distances are measured, and functions derived from the reflectance values at a plurality of wavelengths and light source-detector distances are correlated with a glucose concentration, whereby temperature-induced glycolysis can be tracked.

According to another aspect of the invention, an influence of mechanical and thermal effects occurring when the measurement probe is brought into contact with the skin of a subject can be reduced.

What is claimed is:
1. A method comprising the steps of:
   inducing a change in glucose metabolism in a nutrient capillary in skin by temperature-changed glycolysis;
   measuring a change in localized reflectance light signals at a plurality of light source-detector distances and a plurality of wavelengths over a specific time period after skin-probe contact as a function of a time for which a localized reflectance probe is brought into contact with the skin, said temperature-changed glycolysis causing a change with respect to light attenuation, oxygen consumption in a tissue and concentration of a hemoglobin variant;
   selecting a time window in which a tissue-probe adaptation effect on the signals is minimized and an effect on glycolysis induced by temperature has time dependence, and using a signal measured in the time window for a subsequent calculation;
   calculating one set of functions based on a plurality of localized reflectance values at the plurality of light source-detector distances and the plurality of wave- lengths at a plurality of time intervals in the time window and at least two wavelengths;

deriving a calibration relationship between a combination of the calculated functions and a glucose concentration in a living body; and using the calibration relationship for predicting a glucose concentration in a body fluid in subsequent measurement, wherein at least one function in the plurality of time intervals is associated with a change in oxygen consumption.

2. The method according to claim 1, wherein the calculating step comprises the step of calculating a rate of change in at least one function associated with the time dependence of a temperature change on the localized reflectance values at the plurality of wavelengths and light source-detector distances over the specific time window.

3. The method according to claim 1, wherein the calculating step comprises the step of calculating a degree of change in at least one function associated with a time dependent effect of temperature stimulation on the localized reflectance values at the plurality of wavelengths and light source-detector distances, and the degree of change is calculated for at least one time window and is averaged over adjacent time windows.

4. The method according to claim 1, wherein the wavelengths have different absorption coefficients with respect to oxyhemoglobin and deoxyhemoglobin.

5. The method according to claim 1, wherein data points used in the calculation are present in a time window which starts after a predetermined time from the skin-probe contact.

6. A noninvasive measurement apparatus comprising:

a unit which modulates a temperature of a localized reflectance optical probe, when the probe has been brought into contact with skin to a temperature substantially different from a normal temperature of the skin for inducing a change in temperature of a tissue in a vicinity of the probe and up to a depth of the skin surrounded by a skin vascular system;

a unit which measures a change in localized reflectance light signals at a plurality of light source-detector distances and a plurality of wavelengths over a specific time period after skin-probe contact as a function of a time for which a localized reflectance probe is brought into contact with the skin;

a unit which selects a time window in which a tissue-probe adaptation effect on the signals is minimized, and uses a signal measured in the time window for a subsequent calculation;

a unit which calculates one set of functions based on a plurality of localized reflectance values at the plurality of light source-detector distances and the plurality of wavelengths at a plurality of time intervals in the time window and at least two wavelengths;

a unit which derives a calibration relationship between a combination of the calculated functions and a glucose concentration in a living body; and a unit which uses the calibration relationship for predicting a glucose concentration in a body fluid in subsequent measurement, wherein at least one function in the plurality of time intervals is associated with a change in oxygen consumption.

7. A method, comprising:

inducing a change in glucose metabolism in a nutrient capillary in the skin by temperature-changed glycolysis;

measuring a change in localized reflectance light signals at a plurality of light source-detector distances and a plurality of wavelengths over a specific period of time after skin-probe contact as a function of a time for which a localized reflectance probe is in contact with the skin to determine an oxygen consumption in a tissue and a concentration of a hemoglobin variant with respect to light attenuation;

selecting a time window in the period of time in which a tissue-probe adaptation effect on the localized reflectance light signals is minimized and an effect on the temperature-changed glycolysis has time dependence, and carrying out a subsequent calculation based on a signal measured in the time window;

calculating one set of functions based on a plurality of localized reflectance values at the plurality of light source-detector distances and the plurality of wavelengths at a plurality of time intervals in the time window and at least two wavelengths;

deriving a calibration relationship between a combination of the functions calculated in the step of calculating and a glucose concentration in a living body; and predicting a glucose concentration in a body fluid based on the calibration relationship;

wherein at least one function in the plurality of time intervals is a change in oxygen consumption.

* * * * *